(12) United States Patent
Tanaka et al.

(10) Patent No.: US 12,017,363 B2
(45) Date of Patent: Jun. 25, 2024

(54) CONTINUUM ROBOT CONTROL APPARATUS, CONTINUUM ROBOT CONTROL METHOD AND PROGRAM

(71) Applicant: CANON KABUSHIKI KAISHA, Tokyo (JP)

(72) Inventors: Yusuke Tanaka, Ohta-ku (JP); Kiyoshi Takagi, Koto-ku (JP)

(73) Assignee: Canon Kabushiki Kaisha, Tokyo (JP)

( * ) Notice: Subject to any disclaimer, the term of this patent is extended or adjusted under 35 U.S.C. 154(b) by 844 days.

(21) Appl. No.: 17/045,129

(22) PCT Filed: Mar. 15, 2019

(86) PCT No.: PCT/JP2019/010827
§ 371 (c)(1),
(2) Date: Oct. 2, 2020

(87) PCT Pub. No.: WO2019/193952
PCT Pub. Date: Oct. 10, 2019

(65) Prior Publication Data
US 2021/0146539 A1    May 20, 2021

(30) Foreign Application Priority Data

Apr. 2, 2018 (JP) .................................. 2018-071076

(51) Int. Cl.
*B25J 9/16* (2006.01)
*A61B 34/00* (2016.01)
(Continued)

(52) U.S. Cl.
CPC .............. *B25J 9/1664* (2013.01); *A61B 34/30* (2016.02); *A61B 34/71* (2016.02); *B25J 9/104* (2013.01); *A61B 2034/301* (2016.02)

(58) Field of Classification Search
CPC .............. A61B 34/71; A61B 2034/301; A61B 2034/306; A61B 2090/064;
(Continued)

(56) References Cited

U.S. PATENT DOCUMENTS 9,254,123 B2 *   2/2016   Alvarez ............. A61B 1/00078
2010/0030023 A1 *   2/2010   Yoshie ................ A61B 1/0051
600/117

(Continued)

FOREIGN PATENT DOCUMENTS

EP    2151184 A1    2/2010
JP    2013248119 A    12/2013

OTHER PUBLICATIONS

Kai Xu, et al., An Experimental Kinestatic Comparison between Continuum Manipulators with Structural Variations, 2014, pp. 3258-3264, IEEE, 2014 IEEE International Conference on Robotics & Automation (ICRA), May 31-Jun. 7, 2014, Hong Kong, China.

*Primary Examiner* — Adam R Mott
*Assistant Examiner* — Sagar Kc
(74) *Attorney, Agent, or Firm* — Canon U.S.A., Inc. IP Division

(57) ABSTRACT

The present invention provides a mechanism which can avoid narrowing of a range in which a continuum robot can be driven and suppress damage to the continuum robot and an object. A continuum robot control apparatus controlling an operation of a continuum robot having a bendable portion bending in response to driving of at least some of a plurality of wires includes an external force estimating unit configured to estimate an external force applied to the bendable portion based on compressive/tensile forces applied to two or more wires of the plurality of wires, and a driving control
(Continued)

unit configured to control driving of the wires to be driven based on the external force estimated by the external force estimating unit.

23 Claims, 17 Drawing Sheets

(51) Int. Cl.
  *A61B 34/30* (2016.01)
  *B25J 9/10* (2006.01)
(58) Field of Classification Search
  CPC .... A61B 2090/065; A61B 34/30; B25J 9/104; B25J 9/1664
  See application file for complete search history.

(56) References Cited

U.S. PATENT DOCUMENTS

| 2013/0131868 | A1* | 5/2013 | Rucker | B25J 9/1625 |
| --- | --- | --- | --- | --- |
| | | | | 700/262 |
| 2013/0226350 | A1* | 8/2013 | Bergelin | A61H 1/0288 |
| | | | | 2/160 |
| 2014/0350462 | A1* | 11/2014 | Ataollahi | A61B 1/00073 |
| | | | | 604/95.04 |
| 2015/0088161 | A1* | 3/2015 | Hata | A61B 1/009 |
| | | | | 606/130 |
| 2015/0313619 | A1* | 11/2015 | Tadano | A61B 34/71 |
| | | | | 606/130 |
| 2016/0016319 | A1* | 1/2016 | Remirez | A61B 34/71 |
| | | | | 74/490.04 |
| 2017/0182659 | A1* | 6/2017 | Simaan | B25J 9/1602 |
| 2020/0000536 | A1* | 1/2020 | Yakimovich | B25J 19/02 |

\* cited by examiner

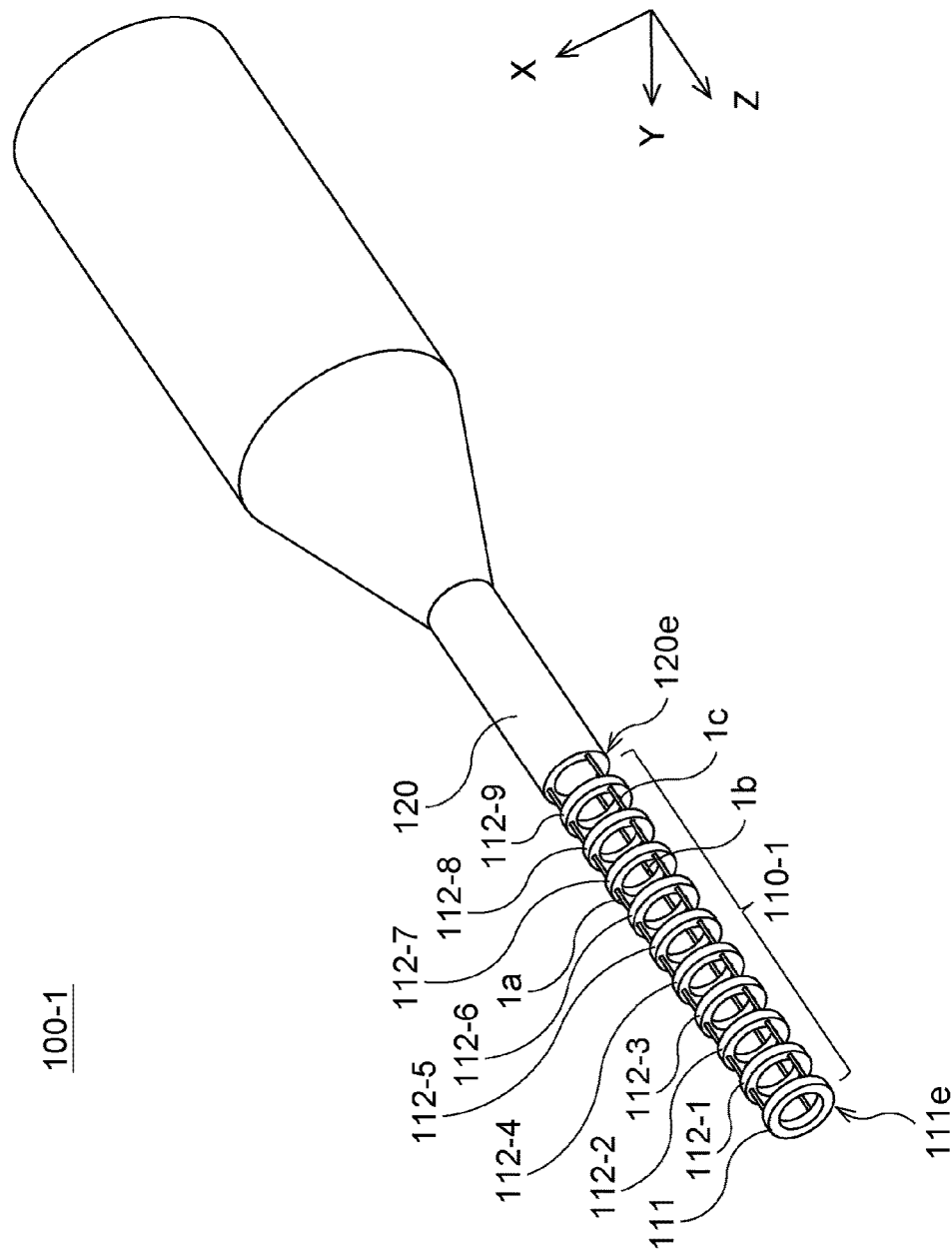
[Fig. 1]

[Fig. 2]
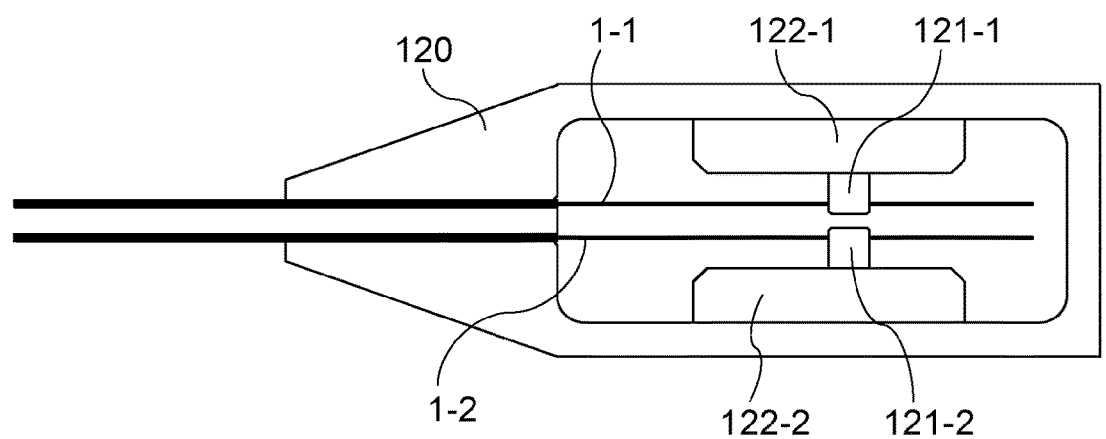
[Fig. 3]
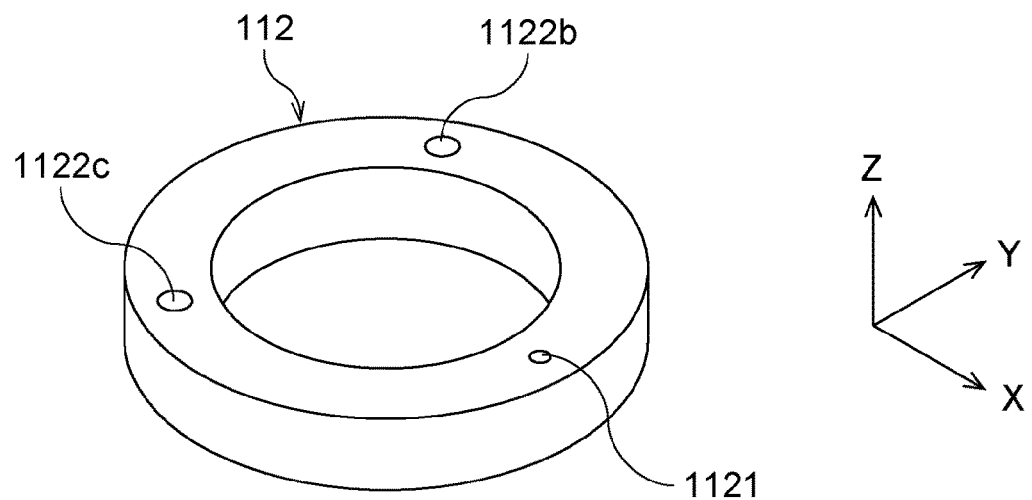

[Fig. 4]
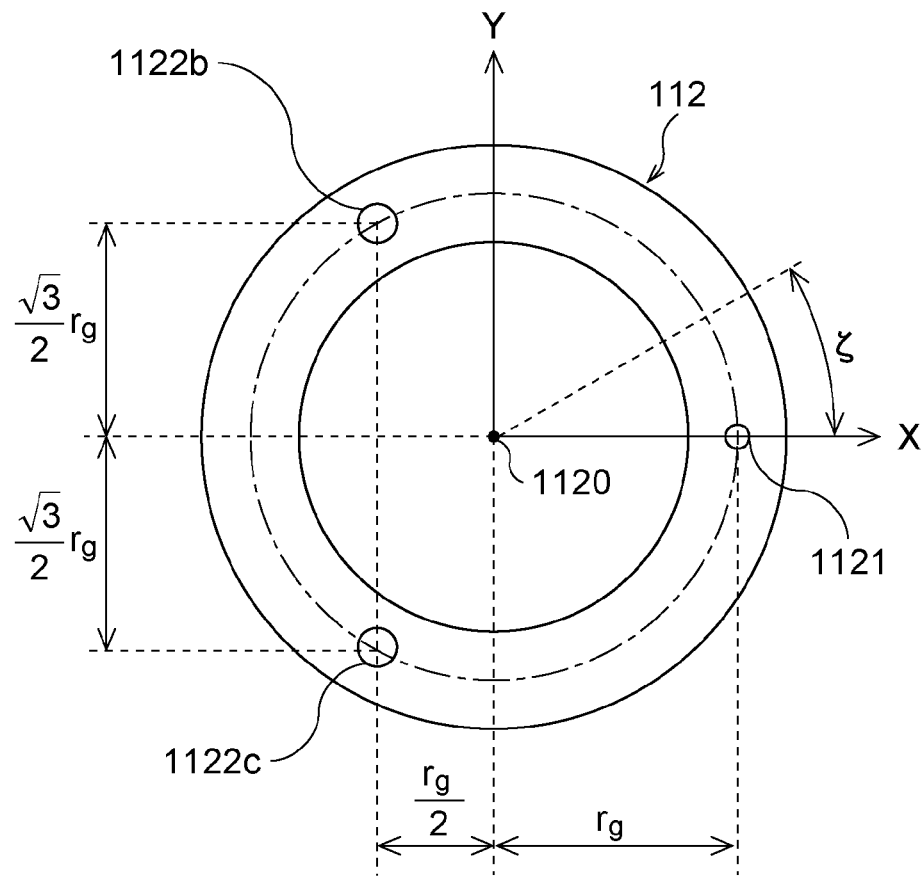
[Fig. 5]
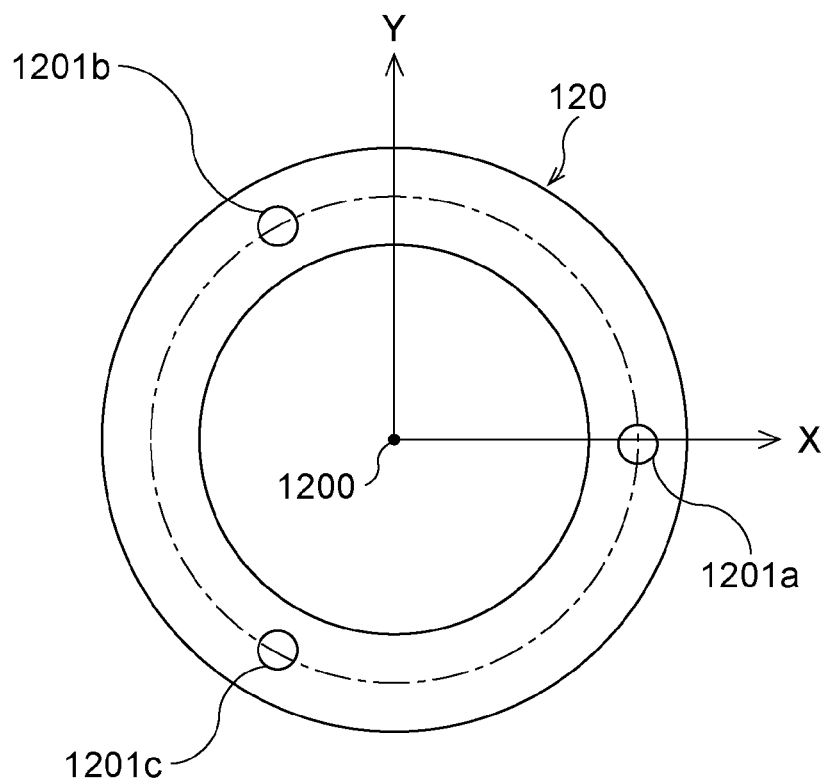

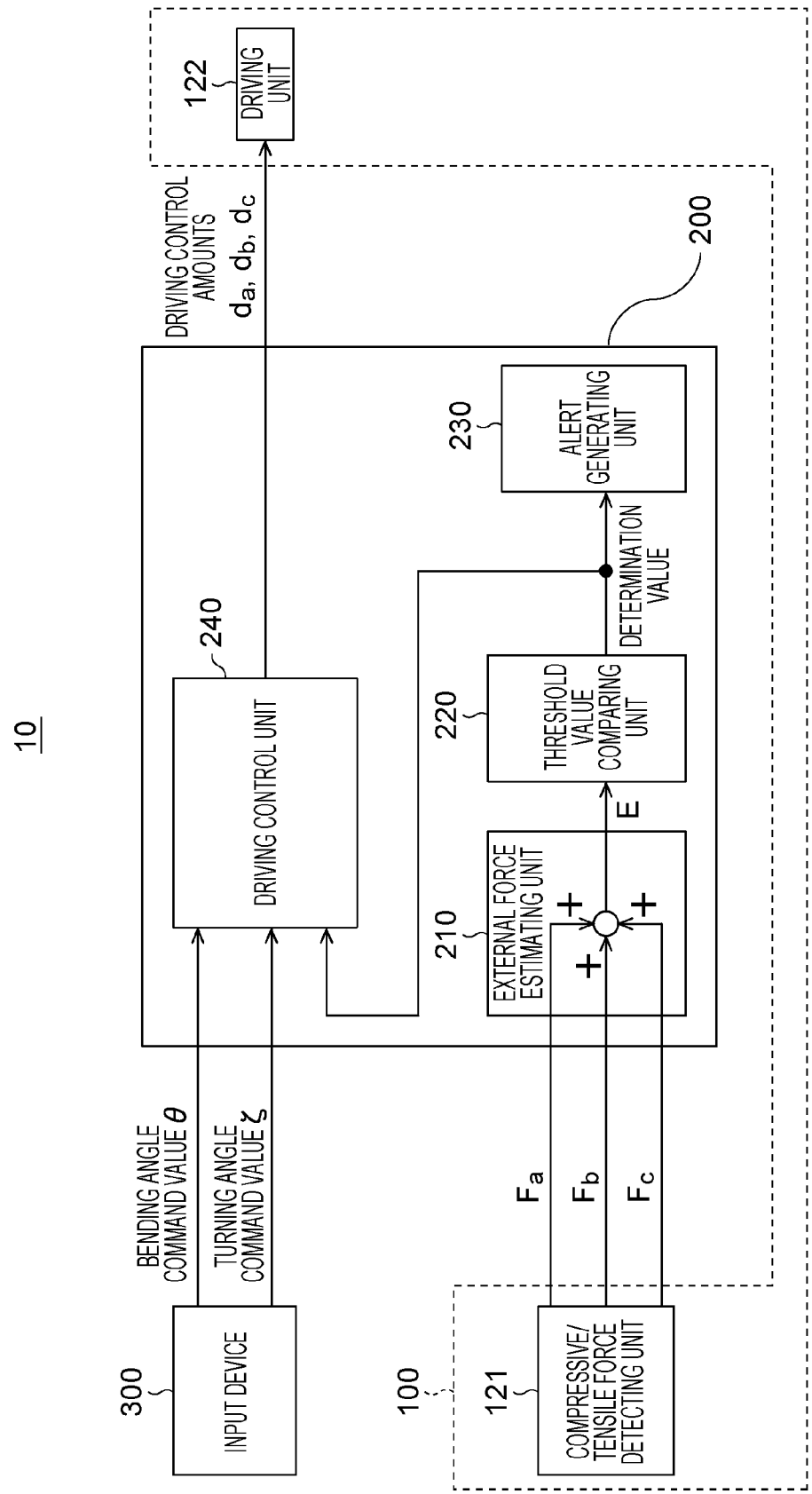
[Fig. 6]

[Fig. 7]
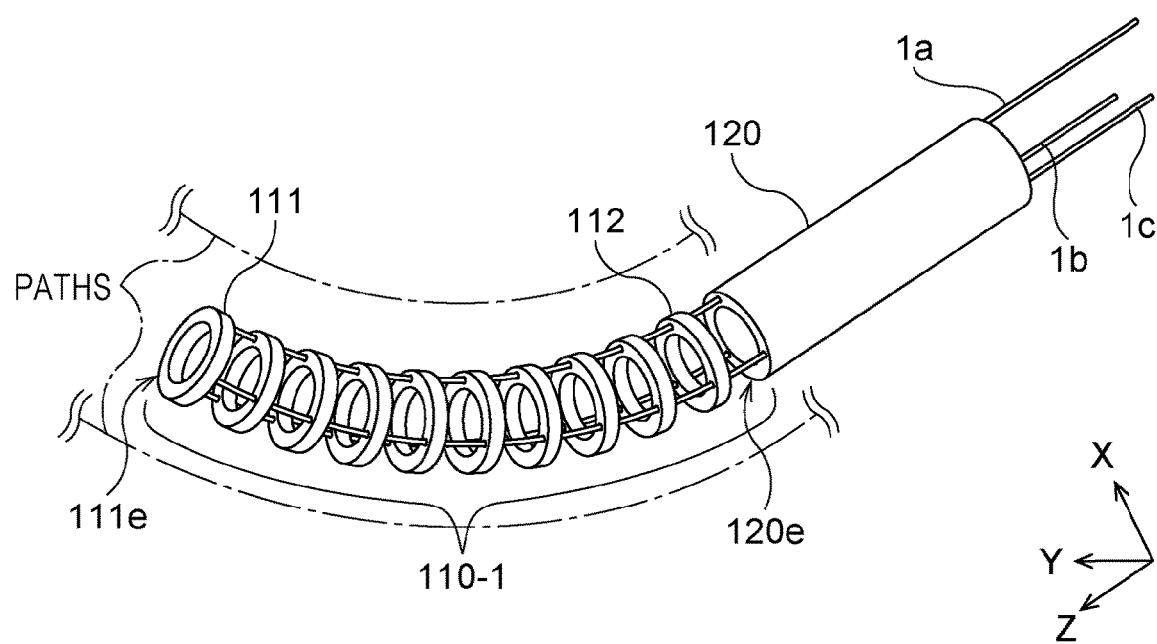

[Fig. 8]
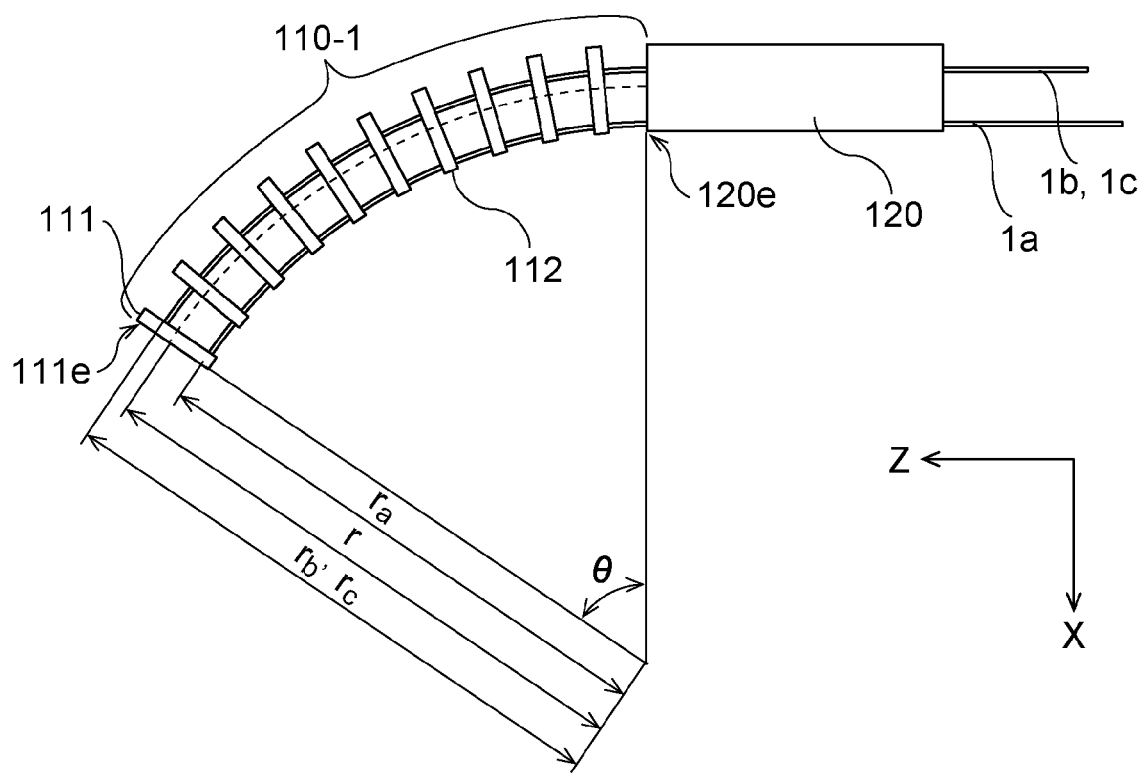

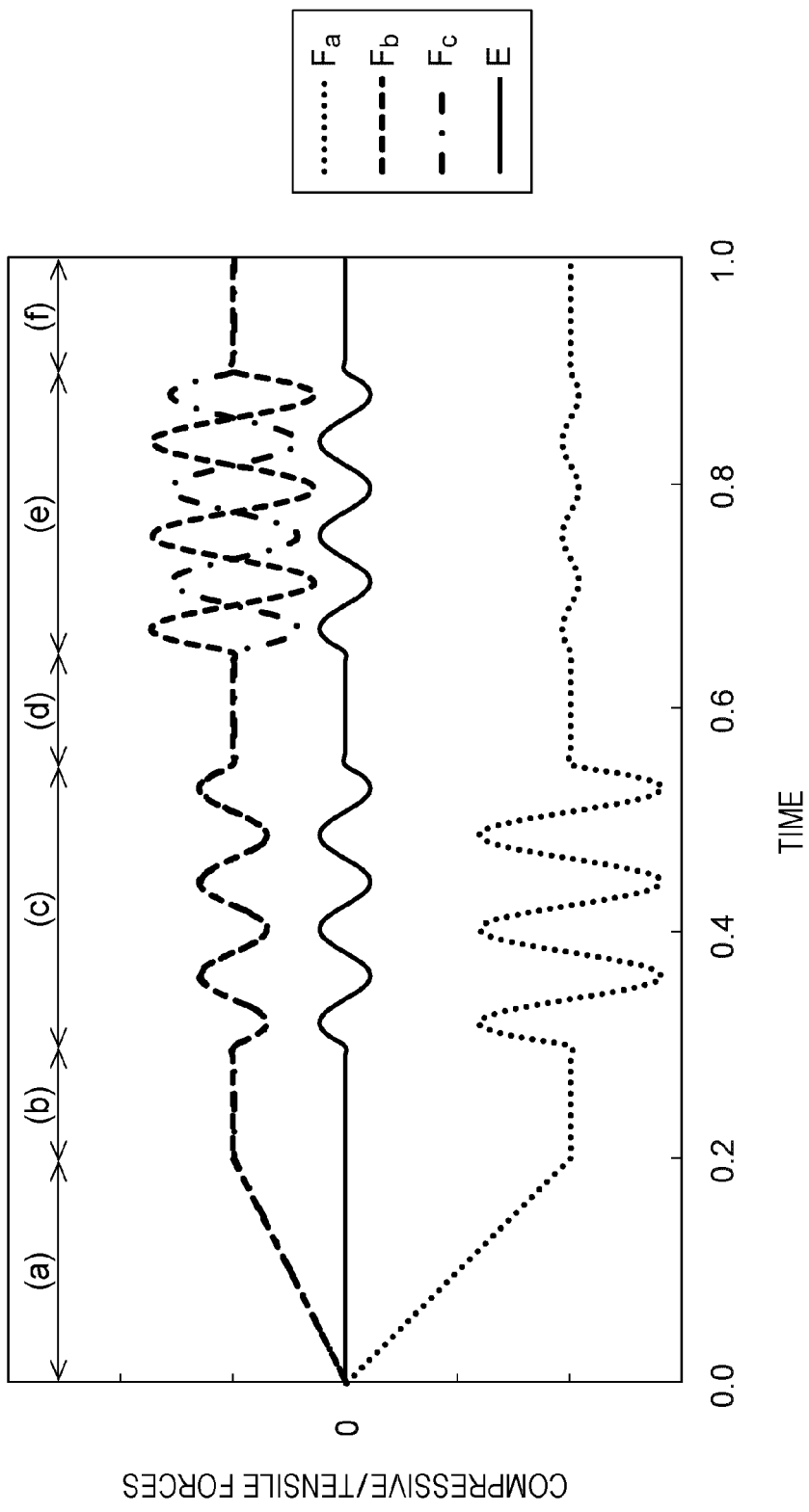
[Fig. 10]

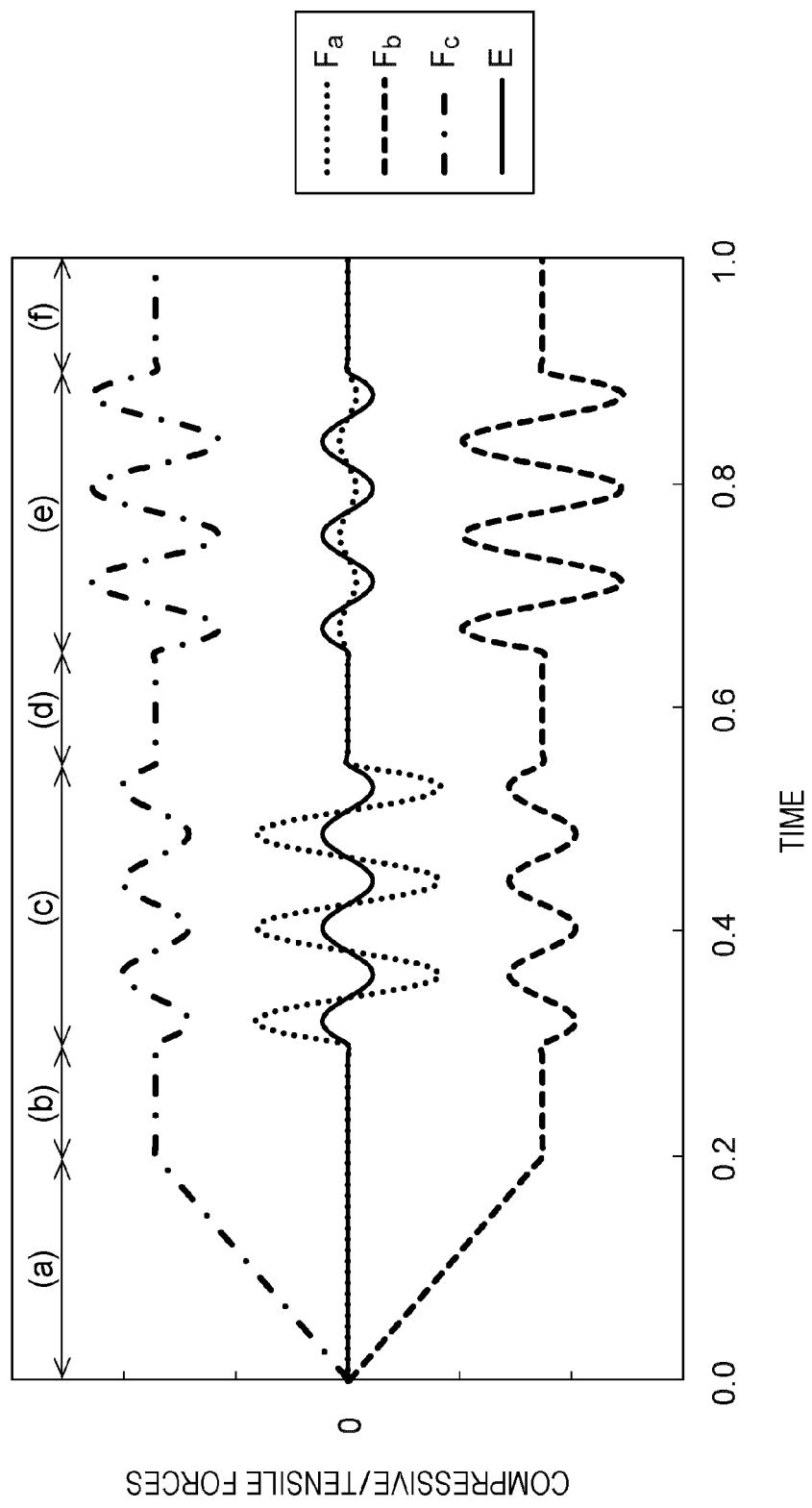
[Fig. 11]

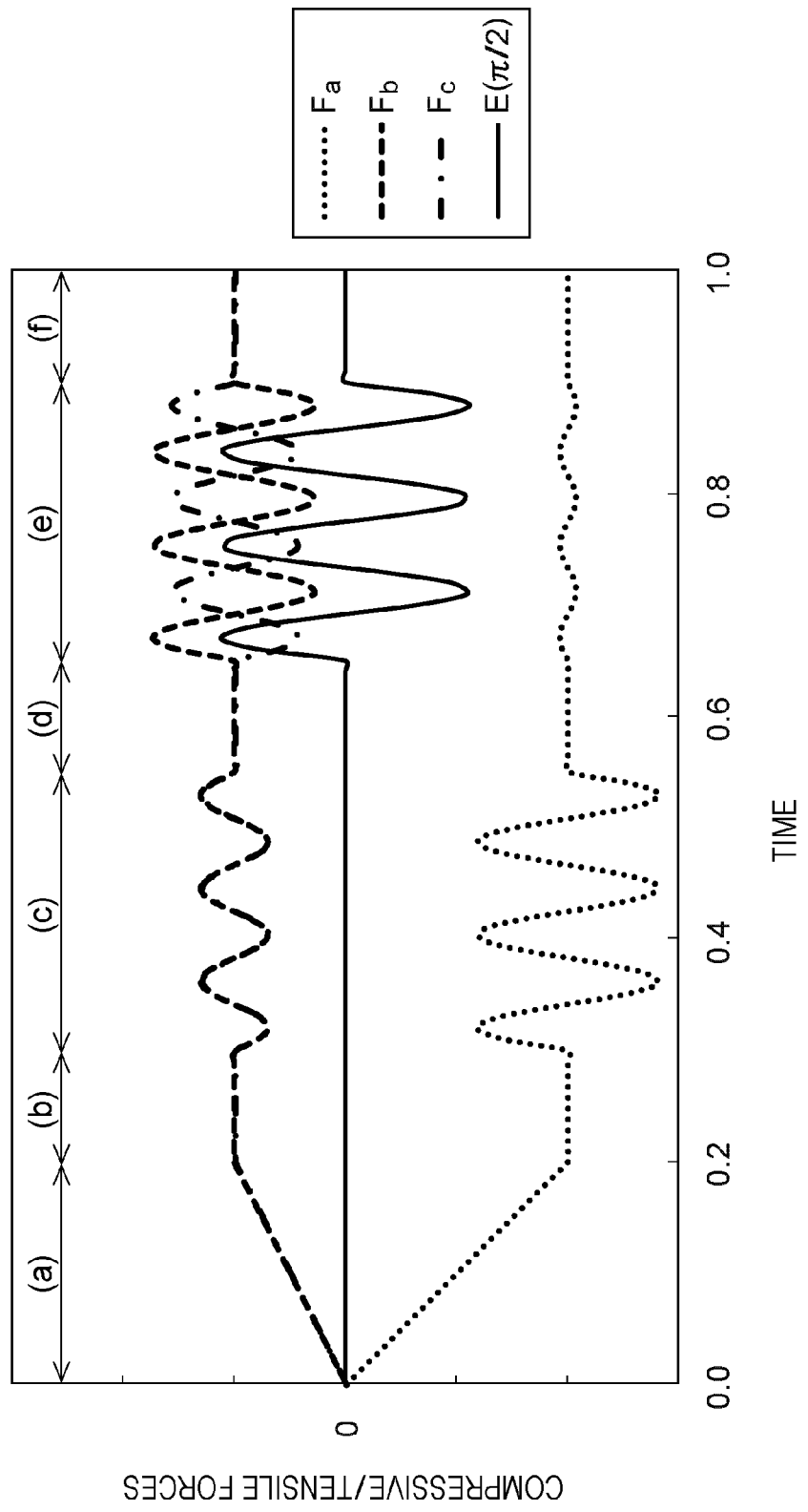
[Fig. 12]

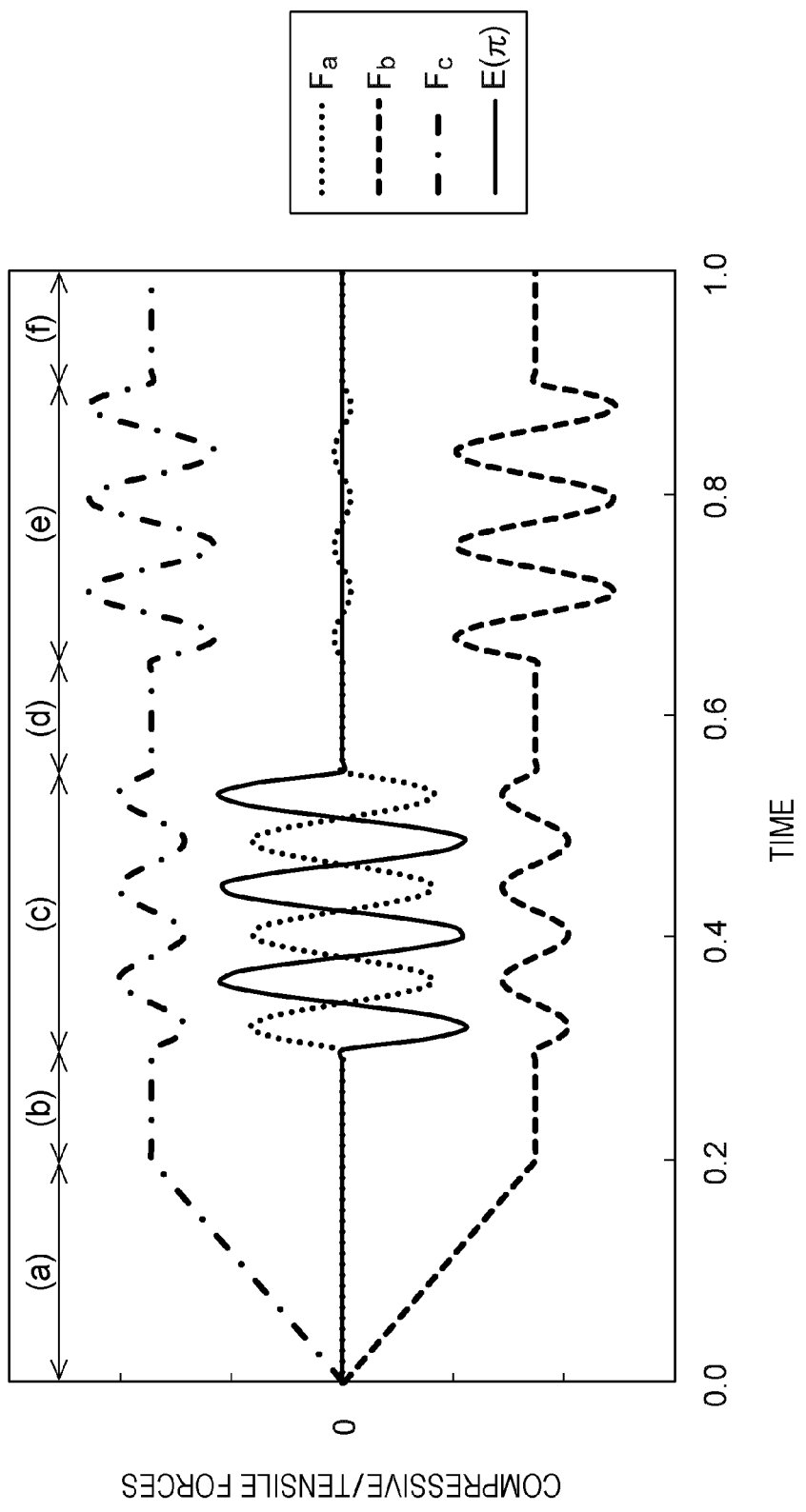
[Fig. 13]

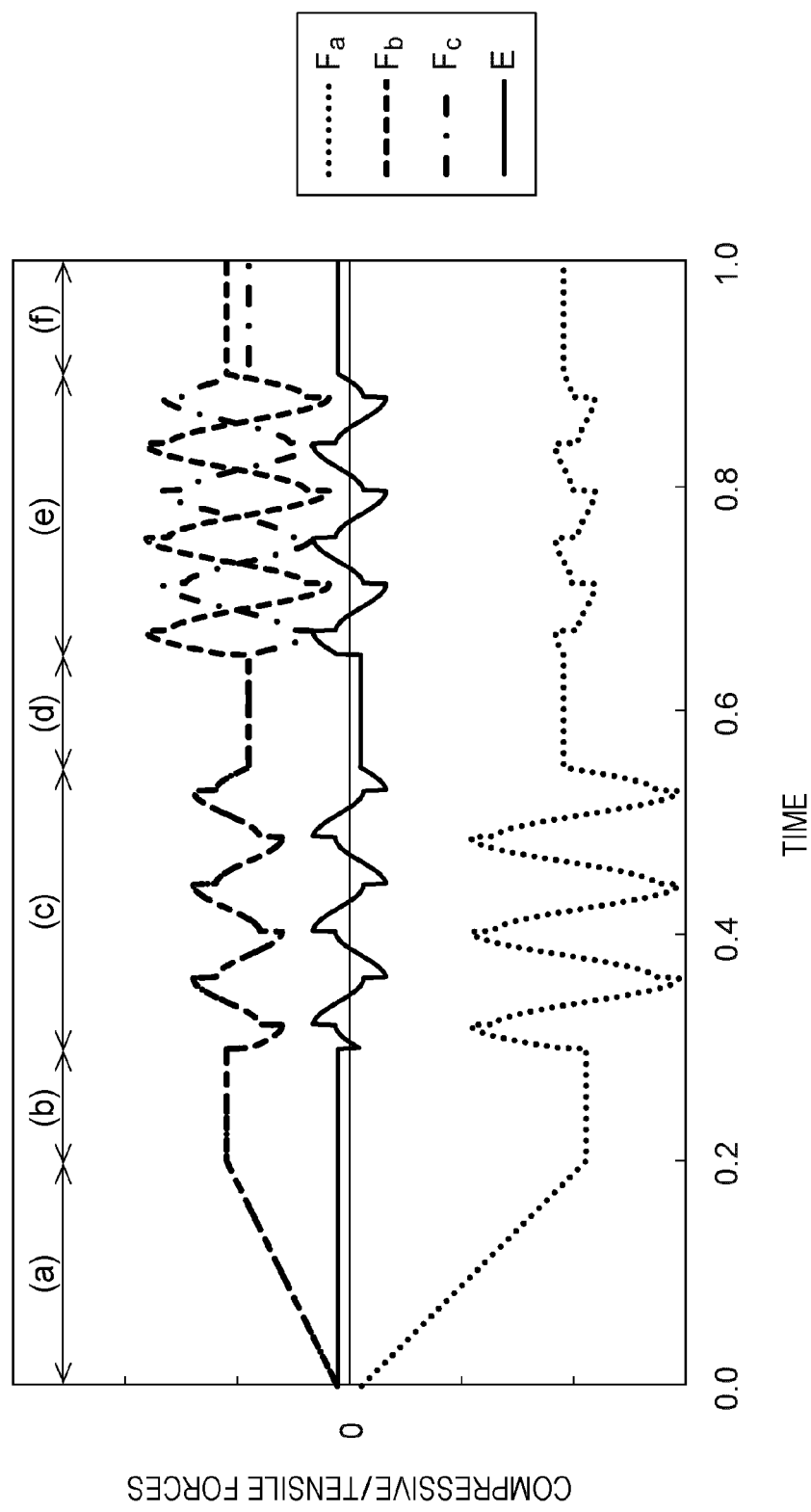
[Fig. 14]

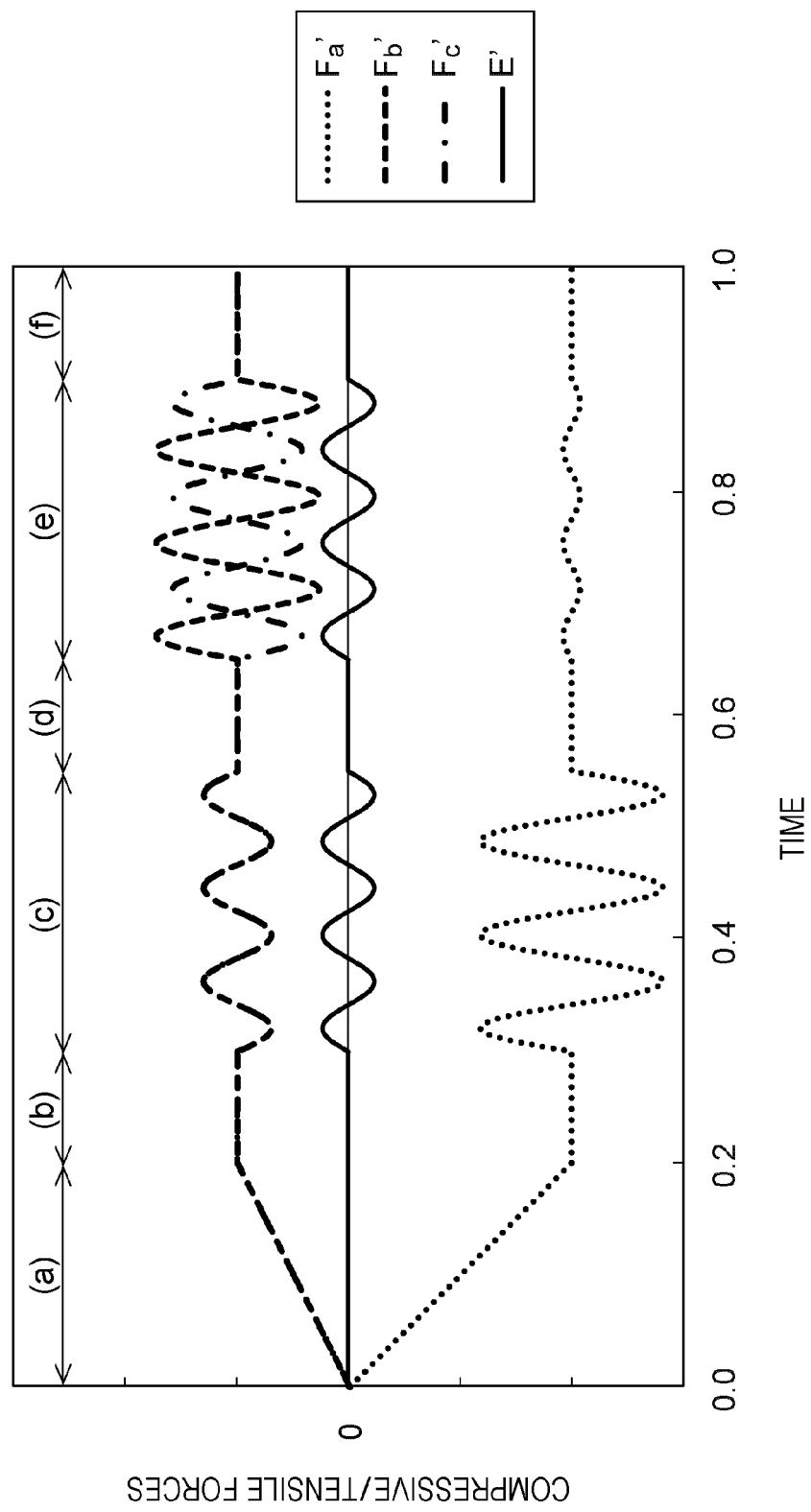
[Fig. 15]

[Fig. 16]
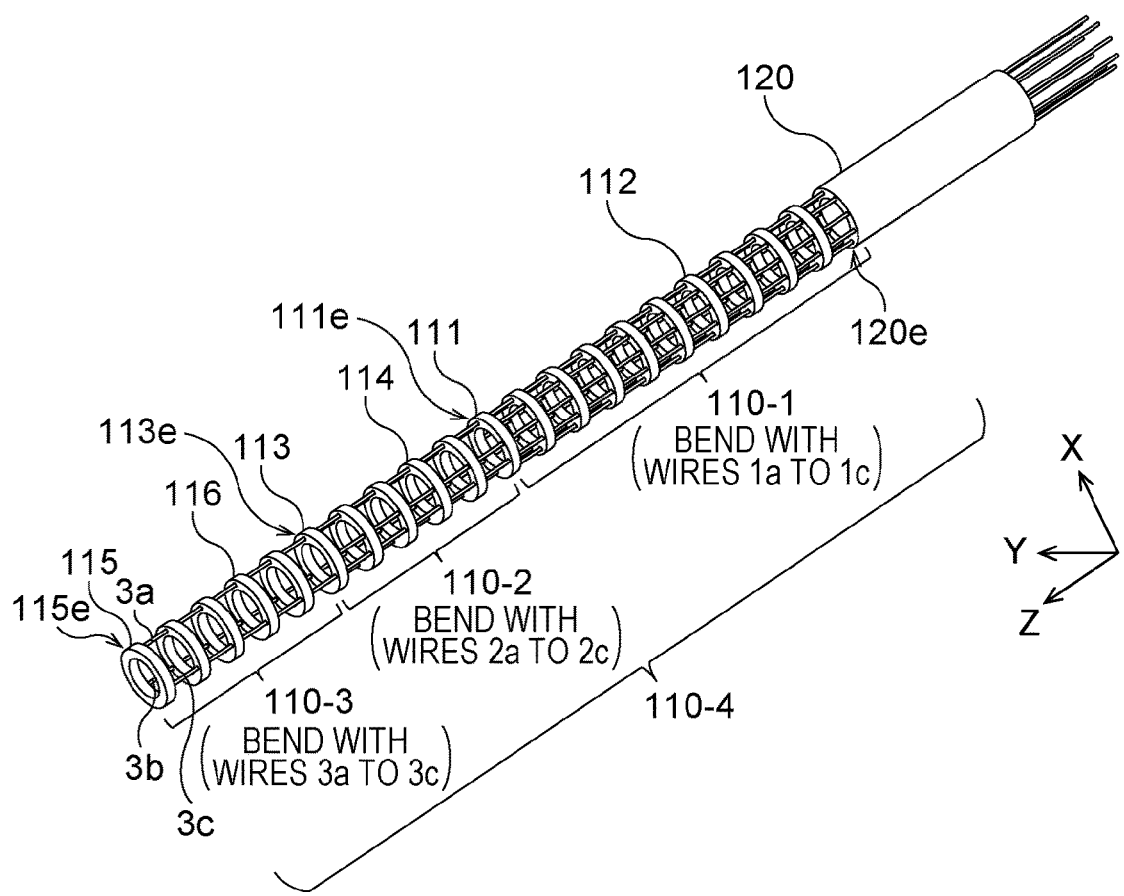

[Fig. 17]
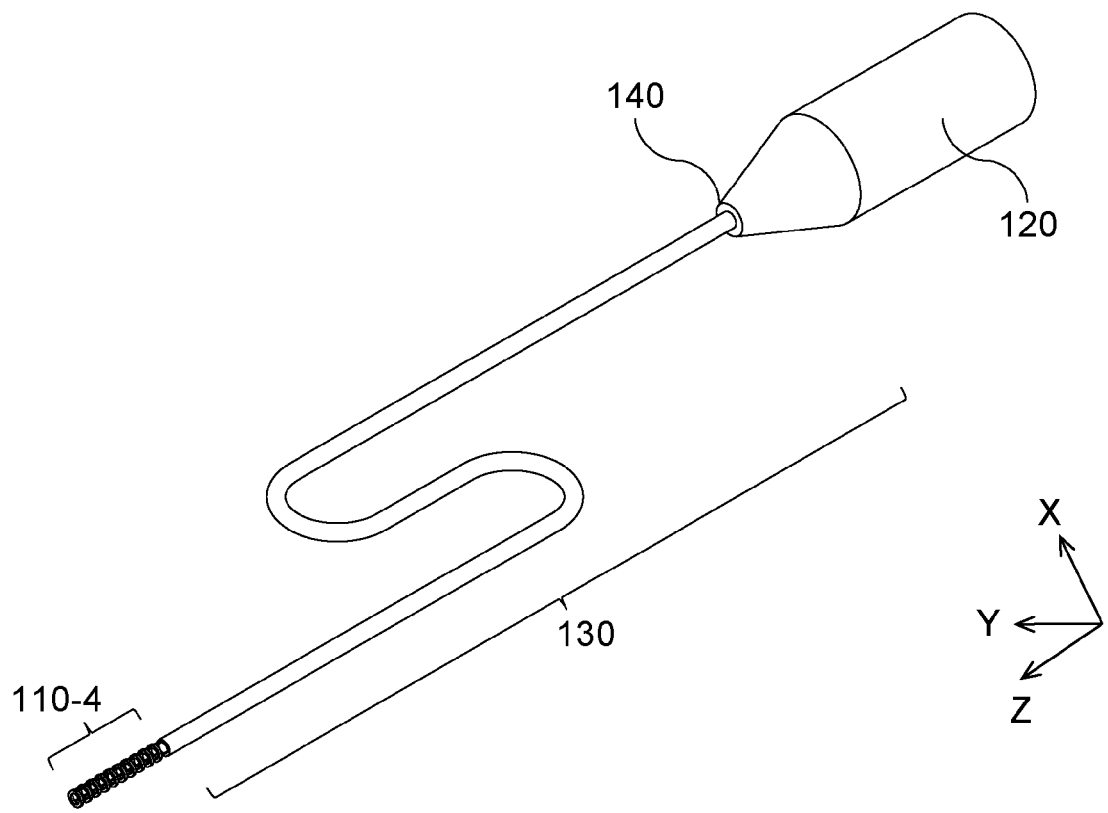

[Fig. 18]
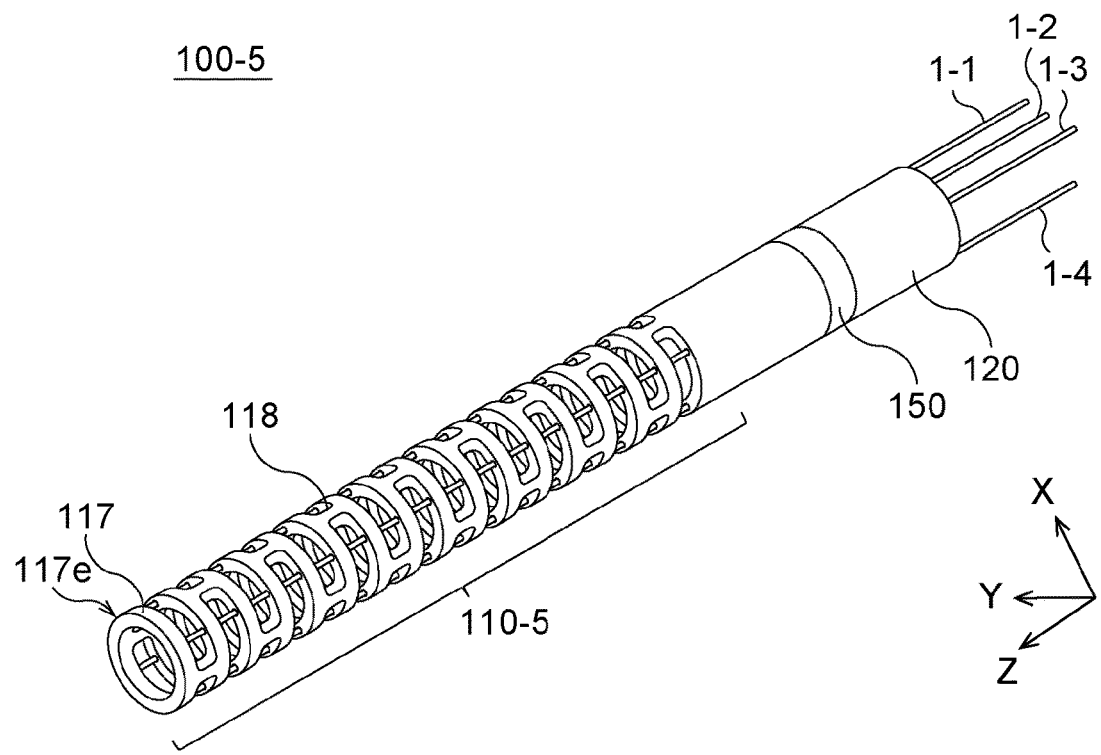
[Fig. 19]
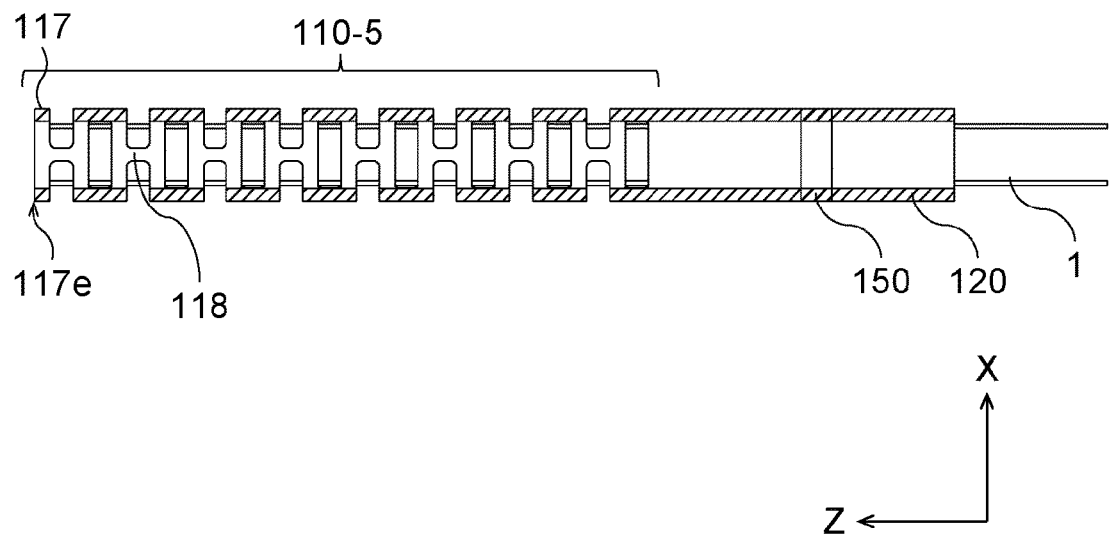

[Fig. 20]
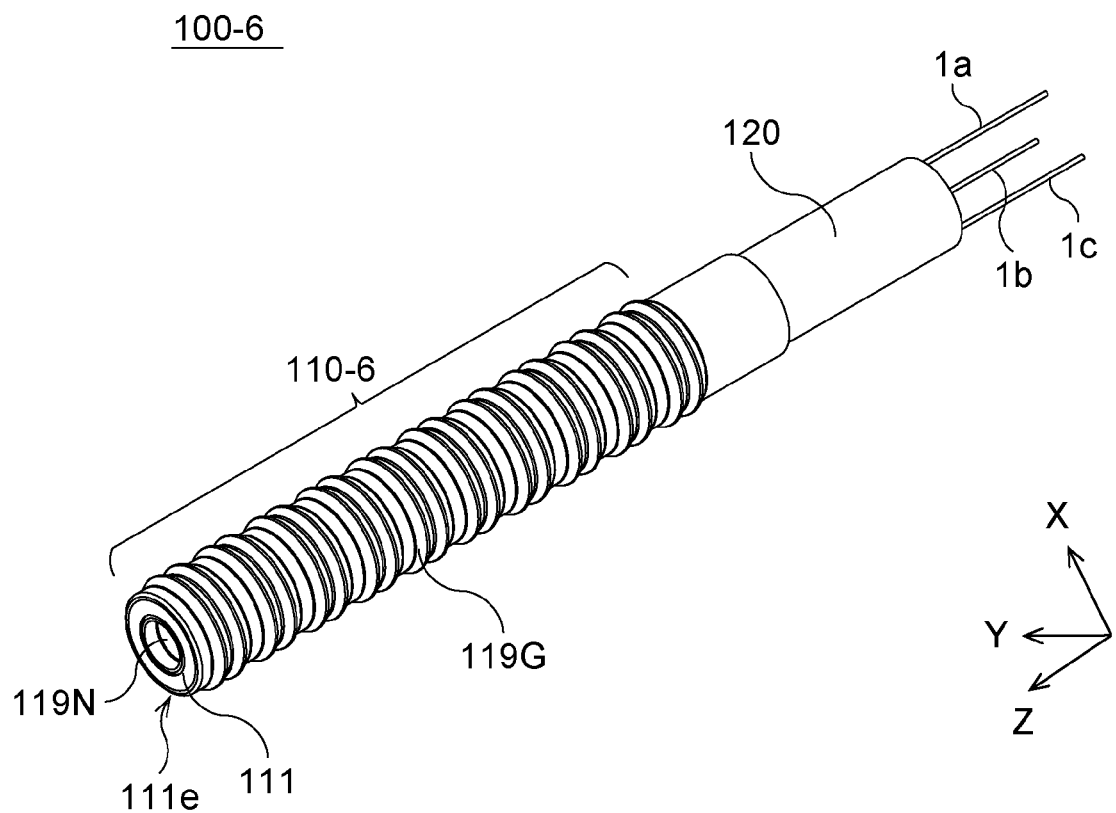
[Fig. 21]
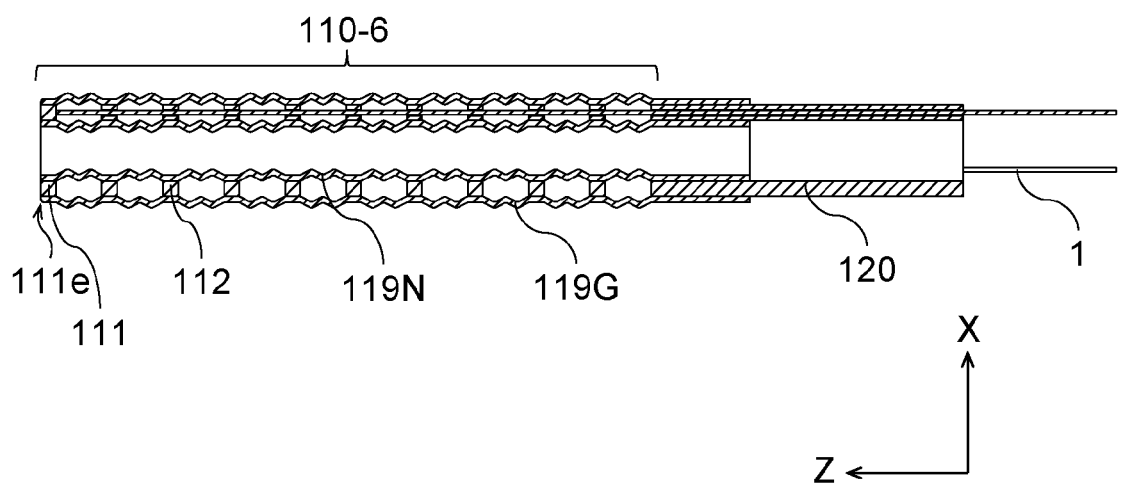

CONTINUUM ROBOT CONTROL APPARATUS, CONTINUUM ROBOT CONTROL METHOD AND PROGRAM

TECHNICAL FIELD

The present invention relates to a continuum robot control apparatus and a continuum robot control method controlling operations of a continuum robot having a bendable portion bending in response to driving of wires therein and a program causing a computer to function as the continuum robot control apparatus.

BACKGROUND ART

A continuum robot includes a bendable portion having a flexible structure that is deformed to control the shape of the continuum robot. The continuum robot is superior to a rigid link robot including a rigid link, for example, because the continuum robot is movable along a predetermined path even in a narrow space or in an environment having objects scattered about by which the rigid link robot may be caught. Due to this feature, continuum robots are expected to be applied to instruments in the medical field such as a sheath of an endoscope and a catheter and robots for hazardous situations such as a rescue robot.

As an example of such a continuum robot, NPL 1 discloses a continuum robot having a bendable portion that bends in response to driving of wires therein.

A continuum robot can also invade a path within a fragile object because it has substantial softness. However, when the continuum robot and the object are brought into contact, high load may be applied to both of them, and they may be damaged. As an example of a technique for avoiding this, for example, PTL 1 discloses a technique in which, even when excessive load is applied to a deformable portion capable of being deformed by wires driven by driving force, a driving unit disconnects wires and the driving force so that damage such as cutting of the wires can be suppressed.

CITATION LIST

Patent Literature

PTL 1: Japanese Patent Laid-Open No. 2013-248119

Non Patent Literature

NPL 1: K. Xu, M. Fu, and J. Zhao, "An Experimental Kinestatic Comparison between Continuum Manipulators with Structural Variations," in IEEE International Conference on Robotics and Automation (ICRA), Hong Kong, China, 2014, pp. 3258-3264

SUMMARY OF INVENTION

Technical Problem

A conventional wire-driven continuum robot generally applies a method which, in a case where a load detected by a load detecting unit provided on each driven wire exceeds a threshold value, disconnects driving force to the driven wire.

However, the driven wire is influenced by not only driving force that bends a bendable portion of the continuum robot but also an external force caused by contact between the continuum robot and an object. Therefore, a method which detects a load on a single driven wire and compares it with a threshold value as in PTL 1 narrows a range in which the continuum robot can be driven when the threshold value is lowered while, when the threshold value is increased, the influence of the external force may not be detected. As a result, an excessive load may be applied between the continuum robot and the object, and they may be damaged. In other words, in the conventional technique, it is difficult to avoid narrowing of the range in which the continuum robot can be driven and to suppress damage to the continuum robot and the object.

The present invention was made in view of such issues and can provide a mechanism which can avoid narrowing of a range in which a continuum robot can be driven and can suppress damage to the continuum robot and an object.

Solution to Problem

A continuum robot control apparatus controlling an operation of a continuum robot having a bendable portion bending in response to driving of at least some of a plurality of wires includes an estimating unit configured to estimate an external force applied to the bendable portion based on a tensile force applied to two or more wires of the plurality of wires, and a driving control unit configured to control driving of the wires to be driven based on the external force estimated by the estimating unit.

The present invention includes a continuum robot control method by the continuum robot control apparatus and a program causing a computer to function as the units in the continuum robot control apparatus.

Advantageous Effects of Invention

According to the present invention, reduction of the range for driving the continuum robot can be avoided while damage to the continuum robot and an object can be suppressed.

Further features of the present invention will become apparent from the following description of exemplary embodiments with reference to the attached drawings.

BRIEF DESCRIPTION OF DRAWINGS

FIG. 1 is a diagram illustrating an example of an outer appearance configuration of a continuum robot according to a first embodiment of the present disclosure.

FIG. 2 is a diagram illustrating an example of an internal configuration of a support mechanism illustrated in FIG. 1.

FIG. 3 is a diagram for explaining a relationship between a guiding member and wires illustrated in FIG. 1.

FIG. 4 is a diagram for explaining a relationship between the guiding member and the wires illustrated in FIG. 1.

FIG. 5 is a diagram for explaining the support mechanism and the wires illustrated in FIG. 1.

FIG. 6 is a diagram illustrating an example of a schematic configuration of a continuum robot control system including a continuum robot control apparatus according to the first embodiment of the present disclosure.

FIG. 7 is a diagram illustrating a state of the continuum robot in a case where a bendable portion illustrated in FIG. 1 is bent in a +X axis direction according to the first embodiment of the present disclosure.

FIG. 8 is a cross section view taken at an XZ plane of the continuum robot illustrated in FIG. 7.

FIG. 10 is a diagram illustrating time changes of compressive/tensile forces of wires and an evaluation value when the bendable portion is bent in an X axis direction under a condition that an external force acts on the bendable portion according to the first embodiment of the present disclosure.

FIG. 11 is a diagram illustrating time changes of the compressive/tensile forces of the wires and the evaluation value when the bendable portion is bent in a Y axis direction under a condition that the external force acts on the bendable portion according to the first embodiment of the present disclosure.

FIG. 12 is a diagram illustrating time changes of compressive/tensile forces of wires and an evaluation value when a bendable portion is bent in an X axis direction under a condition that an external force acts on the bendable portion according to a second embodiment of the present disclosure.

FIG. 13 is a diagram illustrating time changes of the compressive/tensile forces of the wires and the evaluation value when the bendable portion is bent in a Y axis direction under a condition that the external force acts on the bendable portion according to the second embodiment of the present disclosure.

FIG. 14 is a diagram illustrating time changes of compressive/tensile forces of wires and an evaluation value when a bendable portion bends in an X axis direction and receives an external force in a system considering friction of the bendable portion according to a third embodiment of the present disclosure.

FIG. 15 is a diagram illustrating time changes of compressive/tensile forces and an evaluation value corrected (compensated) by using Expression (34) to Expression (36) in the system considering friction of the bendable portion according to the third embodiment of the present disclosure.

FIG. 16 is a diagram illustrating an example of an outer appearance configuration of a continuum robot according to a fourth embodiment of the present disclosure.

FIG. 17 is a diagram illustrating another example of the outer appearance configuration of the continuum robot according to the fourth embodiment of the present disclosure.

FIG. 18 is a diagram illustrating an example of an outer appearance configuration of a continuum robot according to a fifth embodiment of the present disclosure.

FIG. 19 is a cross section view taken at an XZ plane of the continuum robot illustrated FIG. 18.

FIG. 20 is a diagram illustrating an example of an outer appearance configuration of a continuum robot according to a sixth embodiment of the present disclosure.

FIG. 21 is a cross section view taken at an XZ plane of the continuum robot illustrated in FIG. 20.

DESCRIPTION OF EMBODIMENTS

Figure 9:
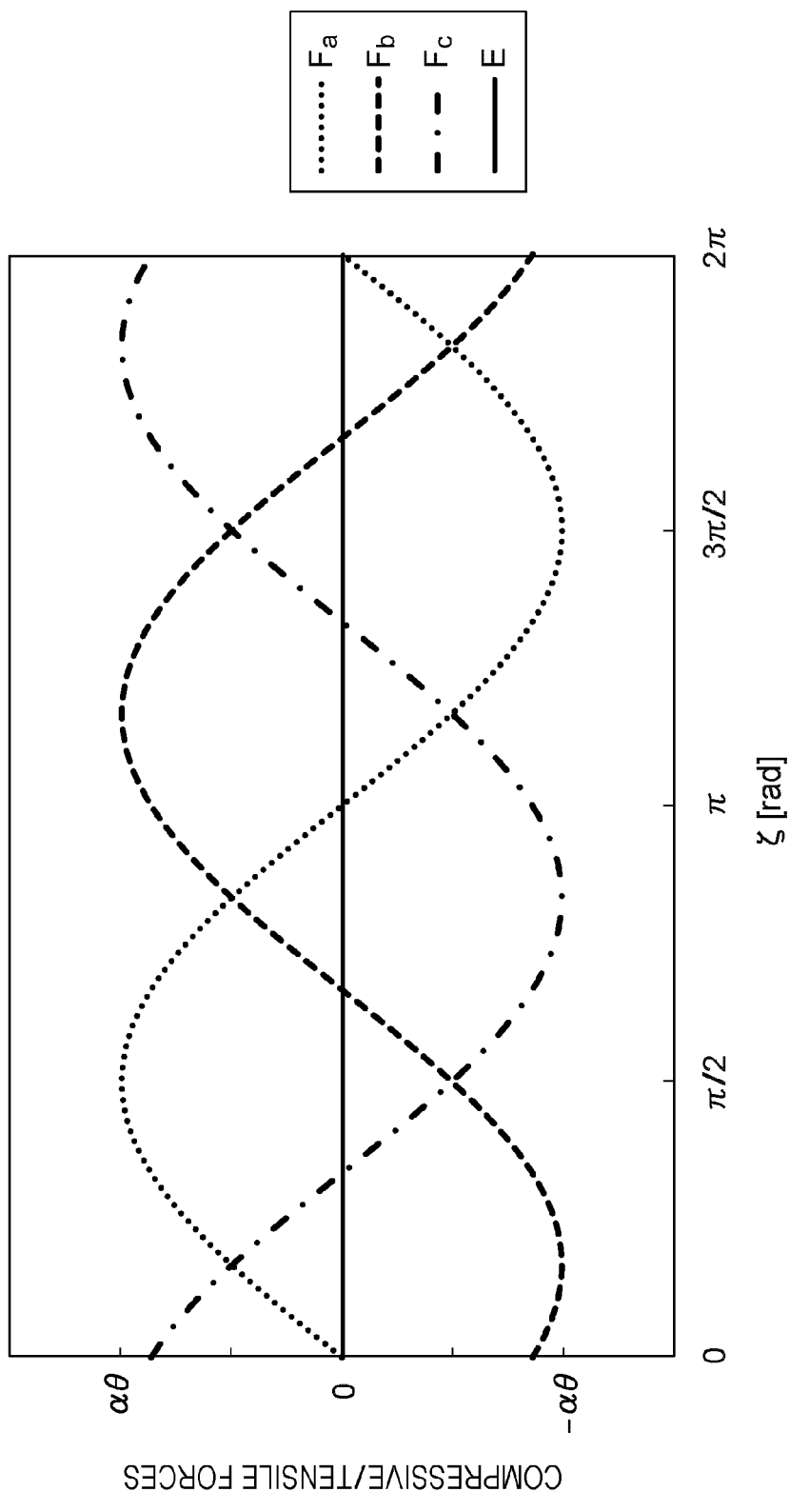
FIG. 9 is a diagram illustrating changes of compressive/tensile forces of wires and evaluation values when an angle for turning the bendable portion is changed with a constant bending angle command value under a condition that no external force acts on the bendable portion according to the first embodiment of the present disclosure.

Embodiments of the present invention will be described in detail below with reference to drawings. More specifically, according to embodiments of the present invention which will be described below, a control system for a continuum robot (also called a continuum manipulator) is applied to a flexible endoscope, for example. A flexible endoscope applied as an example of a continuum robot control system according to embodiments of the present invention is not limited to the medical field but may be applicable in other fields (such as an industrial endoscope configured to observe inside of a pipe) if only the flexible endoscope is any instrument configured to observe inside of a path to and from which a bendable portion of the continuum robot may be inserted and evulsed.

First Embodiment

First of all, a first embodiment of the present invention will be described below.

FIG. 1 is a diagram illustrating an example of an outer appearance configuration of a continuum robot 100 according to a first embodiment of the present invention. Hereinafter, the continuum robot 100 illustrated in FIG. 1 will be called a "continuum robot 100-1" as required. FIG. 1 illustrates an XYZ coordinate system in a three-dimensional space.

The continuum robot 100-1, as illustrated in FIG. 1, includes a wire $1a$, a wire $1b$, a wire $1c$, a bendable portion 110-1, and a support mechanism 120.

Referring to FIG. 1, the wire $1a$, wire $1b$ and wire $1c$ are arranged in a direction parallel with a Z axis direction. The wires $1a$ to $1c$ have ends in the +Z axis direction bonded and fixed at different positions of a tip member 111 and have ends in the −Z axis direction connected to compressive/tensile force detecting units and driving units, each provided for each of the wires, within the support mechanism 120.

The bendable portion 110-1 bends in response to driving of at least some wires 1 of the plurality of wires $1a$ to $1c$. This embodiment assumes here that all wires 1 of the plurality of wires $1a$ to $1c$ are driven to bend the bendable portion 110-1. The bendable portion 110-1 includes the tip member 111 and a plurality of guiding members 112-1 to 112-9. Here, in the example illustrated in FIG. 1, the bendable portion 110-1 extends from an end $111e$ of the tip member that is an end in the +Z axis direction of the tip member 111 to an end $120e$ of the support mechanism that is an end in the +Z axis direction of the support mechanism 120. Hereinafter, "guiding member 112" is simply used as a representative of the guiding member 112-1 to 112-9 for description. The tip member 111 has a ring shape with the Z axis direction as a center axis, and the wires $1a$ to $1c$ are bonded and fixed at positions different from each other in the tip member 111, as illustrated in FIG. 1.

Next, an internal structure of the support mechanism 120 illustrated in FIG. 1 will be described.

FIG. 2 is a diagram illustrating an example of an internal structure of the support mechanism 120 illustrated in FIG. 1. In FIG. 1 and FIG. 2, like numbers refer to like parts. Referring to FIG. 2, the wire 1-1 is any one wire of the wires $1a$ to $1c$ illustrated in FIG. 1 and is the wire $1a$, for example. A wire 1-2 is any one wire of the wires $1a$ to $1c$ illustrated in FIG. 1, is different from the wire 1-1 illustrated in FIG. 2, and is the wire $1b$, for example. FIG. 2 does not illustrate one wire, such as the wire $1c$, of the wires $1a$ to $1c$ illustrated in FIG. 1 because of space limitations.

The compressive/tensile force detecting unit 121 is configured to detect a compressive/tensile force applied to the wire 1 connected thereto. A compressive force and a tensile force are collectively called "compressive/tensile force" herein. FIG. 2 illustrate a compressive/tensile force detecting unit 121-1 configured to detect a compressive/tensile force applied to the wire 1-1 (or the wire $1a$ illustrated in FIG. 1, for example) and a compressive/tensile force detecting unit 121-2 configured to detect a compressive/tensile force applied to the wire 1-2 (or the wire $1b$ illustrated in FIG. 1, for example). FIG. 2 does not illustrate a compressive/tensile force detecting unit 121-3 configured to detect a compressive/tensile force applied to the wire (or the wire 1c, for example) not illustrated in FIG. 2 of the wires 1a to 1c illustrated in FIG. 1, but the compressive/tensile force detecting unit 121-3 is provided within the support mechanism 120 according to this embodiment. Hereinafter, "compressive/tensile force detecting unit 121" is simply used as a representative of the compressive/tensile force detecting units 121-1 to 121-3 for description.

A driving unit 122 is connected to the wire 1 through, for example, the compressive/tensile force detecting unit 121 and drives the wire 1 under control of a continuum robot control apparatus (continuum robot control apparatus 200 illustrated in FIG. 6), which will be described below. FIG. 2 illustrates a driving unit 122-1 configured to drive the wire 1-1 (wire 1a illustrated in FIG. 1, for example) and a driving unit 122-2 configured to drive the wire 1-2 (wire 1b illustrated in FIG. 1, for example). A driving unit 122-3, not illustrated in FIG. 2, configured to drive the wire (wire 1c, for example) not illustrated in FIG. 2 of the wires 1a to 1c illustrated in FIG. 1 is provided within the support mechanism 120 according to this embodiment. Hereinafter, "driving unit 122" is simply used as a representative of the driving units 122-1 to 122-3 for description.

Next, a relationship between the guiding member 112 and the wires 1a to 1c illustrated in FIG. 1 will be described. FIG. 3 and FIG. 4 are drawings for explaining a relationship between the guiding member 112 and the wires 1a to 1c illustrated in FIG. 1.

The guiding member 112 has a ring shape with the Z axis direction as a center axis as illustrated in FIG. 3. The guiding member 112 has a fixing hole 1121, a guiding hole 1122b and a guiding hole 1122c, which are through-holes in the Z axis direction as illustrated in FIG. 3. For example, according to this embodiment, the wire 1a is fixed to the fixing hole 1121. The wire 1b and 1c, for example, are slidably arranged through the guiding holes 1122b and 1122c.

FIG. 4 is a cross section view taken at an XY plane of the guiding member 112 illustrated in FIG. 3. FIG. 4 illustrates the XY plane about a center axis 1120 in the Z axis direction. As illustrated in FIG. 4, the fixing hole 1121 and the guiding holes 1122b and 1122c in the guiding member 112 are arranged at positions being the apexes of a regular triangle inscribed in a circle having a radius $r_g$ from the center axis 1120. FIG. 4 illustrates the position of the fixing hole 1121 on the X axis.

Next, a relationship between the support mechanism 120 and the wires 1a to 1c illustrated in FIG. 1 will be described. FIG. 5 is a diagram for explaining a relationship between the support mechanism 120 and the wires 1a to 1c illustrated in FIG. 1. More specifically, FIG. 5 is a cross section view taken at an XY plane of the support mechanism 120 illustrated in FIG. 1.

The support mechanism 120 has a cylindrical shape with the Z axis direction as the center axis 1200 as illustrated in FIG. 5. The center axis 1200 in the Z axis direction illustrated in FIG. 5 is identical to the center axis 1120 in the Z axis direction illustrated in FIG. 4. The support mechanism 120 has, as illustrated in FIG. 5, a through-hole 1201a, a through-hole 1201b and a through-hole 1201c corresponding to the holes in the guiding member 112 illustrated in FIG. 4. The wires 1a, 1b and 1c, for example, are slidably arranged through the through-holes 1201a, 1201b and 1201c, respectively. The support mechanism 120 is configured such that the wires 1a, 1b and 1c in the through-hole 1201a, 1201b and 1201c can transmit forces without buckling when the wires 1a, 1b and 1c are driven in the Z axis direction.

FIG. 6 is a diagram illustrating an example of a schematic configuration of a continuum robot control system 10 including the continuum robot control apparatus 200 according to the first embodiment of the present invention.

The continuum robot control system 10 includes the continuum robot 100, the continuum robot control apparatus 200, and an input device 300 as illustrated in FIG. 6. As a configuration of the continuum robot 100, FIG. 6 illustrates the compressive/tensile force detecting unit 121 and the driving unit 122 of the components of the continuum robot 100 illustrated in FIG. 1 without illustrating the other components. Because of space limitations, FIG. 6 collectively illustrates a plurality of the compressive/tensile force detecting units 121 and a plurality of the driving units 122 corresponding to the wires 1a to 1c as one compressive/tensile force detecting unit 121 and one driving unit 122.

The continuum robot control apparatus 200 is a control apparatus configured to control an operation of the continuum robot 100 (continuum robot 100-1 illustrated in FIG. 1 according to this embodiment). The continuum robot control apparatus 200 includes an external force estimating unit 210, a threshold value comparing unit 220, an alert generating unit 230, and a driving control unit 240, as illustrated in FIG. 6.

The external force estimating unit 210 is a component configured to estimate an external force applied to the bendable portion 110 (bendable portion 110-1 illustrated in FIG. 1 according to this embodiment) based on a tensile force (compressive/tensile force) applied to two or more wires 1 of the plurality of wires 1a to 1c. More specifically, in the example illustrated in FIG. 6, the external force estimating unit 210 estimates an external force applied to the bendable portion 110 based on a compressive/tensile force $F_a$ of the wire 1a, a compressive/tensile force $F_b$ of the wire 1b and a compressive/tensile force $F_c$ of the wire 1c detected by the compressive/tensile force detecting unit 121.

The threshold value comparing unit 220 compares the external force estimated by the external force estimating unit 210 and a threshold value and determines whether the external force estimated by the external force estimating unit 210 exceeds the threshold value or not.

The alert generating unit 230 alerts in a case where the alert generating unit 230 receives, from the threshold value comparing unit 220, a determination result (determination value) that the external force estimated by the external force estimating unit 210 exceeds the threshold value. In this case, the alert by the alert generating unit 230 may be implemented by a mode with presentation of a warning indication or a mode with emission of an alert sound or both of the modes, for example.

The driving control unit 240 outputs driving control amounts $d_a$, $d_b$ and $d_c$ to the driving unit 122 in accordance with the determination result (determination value) determined by the threshold value comparing unit 220 based on the external force estimated by the external force estimating unit 210 by using the threshold value to control driving of the wires 1a, 1b and 1c. More specifically, in a case where the driving control unit 240 receives, from the threshold value comparing unit 220, a determination result (determination value) that the external force estimated by the external force estimating unit 210 does not exceed the threshold value, the driving control unit 240 outputs the driving control amounts $d_a$, $d_b$ and $d_c$ to the driving unit 122 based on a command value associated with the bending angle (angle θ illustrated in FIG. 8) of the bendable portion 110 and a command value associated with the turning angle (angle ζ illustrated in FIG. 4) of the bendable portion 110 input from the input device 300 to drive the wires 1a, 1b and 1c. In a case where the driving control unit 240 receives, from the threshold value comparing unit 220, a determination result (determination value) that the external force estimated by the external force estimating unit 210 exceeds the threshold value, the driving control unit 240 outputs the driving control amounts $d_a$, $d_b$ and $d_c$ to the driving unit 122 to stop driving of the wires 1a, 1b and 1c. In other words, in a case where the driving control unit 240 receives, from the threshold value comparing unit 220, a determination result (determination value) that the external force exceeds the threshold value, the controlling of driving based on the bending angle command value and turning angle command value input from the input device 300 is not performed.

The driving unit 122 may drive the wires 1a, 1b and 1c in accordance with the driving control amounts $d_a$, $d_b$ and $d_c$ output from the driving control unit 240.

FIG. 7 is a diagram illustrating a state of the continuum robot 100 in a case where the bendable portion 110-1 illustrated in FIG. 1 is bent in the +X axis direction according to the first embodiment of the present invention. FIG. 8 is a cross section view taken at an XZ plane of the continuum robot 100 illustrated in FIG. 7. In FIG. 1, FIG. 7 and FIG. 8, like numbers refer to like parts, and any repetitive descriptions will be omitted. FIG. 7 also illustrates a path within an object through which the bendable portion 110-1 is to be inserted and evulsed.

Referring to FIG. 8, a bending angle command value after driving is θ, and the length of the bendable portion 110-1 before the driving is L. It is assumed here that the bendable portion 110-1 bends within the XZ plane by keeping a constant curvature. In this case, the length and curvature of the bendable portion 110-1 are defined as the length and curvature of the centerline in the Z axis direction of the shape of the bendable portion 110-1 before it is bent. The driving control amounts in the +Z axis direction for the wires 1a, 1b and 1c are defined as $d_a$, $d_b$ and $d_c$, the radius of curvature of the bendable portion 110-1 is defined as r, and the radius of curvatures of the wires 1a, 1b and 1c are defined as $r_a$, $r_b$ and $r_c$, respectively.

First, a bending operation of the continuum robot 100-1 when the wires 1a, 1b and 1c are driven without application of an external force to the bendable portion 110-1 and compressive/tensile forces applied to the wires 1a, 1b and 1c will be described.

From the matters illustrated in FIG. 4 and FIG. 8, rθ, $r_a$θ, $r_b$θ, and $r_c$θ can be expressed by the following relational expressions (1), (2), (3), and (4).

[Math. 1]

$$r\theta = L \quad (1)$$

$$r_a\theta = (r - r_g)\theta = L + d_a \quad (2)$$

$$r_b\theta = \left(r + \frac{r_g}{2}\right)\theta = L + d_b \quad (3)$$

$$r_c\theta = \left(r + \frac{r_g}{2}\right)\theta = L + d_c \quad (4)$$

From the relationships expressed by Expressions (1) to (4), the driving control amounts $d_a$, $d_b$ and $d_c$ for the wires 1a, 1b and 1c based on the bending angle command value θ are expressed by Expressions (5), (6) and (7).

[Math. 2]

$$d_a = -r_g\theta \quad (5)$$

$$d_b = \frac{r_g\theta}{2} \quad (6)$$

$$d_c = \frac{r_g\theta}{2} \quad (7)$$

Assuming that friction acting between the wire 1 and the guiding member 112 and the support mechanism 120 is ignorable, the compressive/tensile forces $F_a$, $F_b$ and $F_c$ applied to the wires 1a, 1b and 1c, respectively, are in proportion to the bending angle command value θ, which can be expressed by Relational Expressions (8), (9), and (10) below. According to this embodiment, it is assumed that all of the wires 1 have equal flexural rigidity, and a proportionality constant α in the following Expressions (8) to (10) depends on mechanical properties of the structure or constituent materials of the bendable portion 110-1.

[Math. 3]

$$F_a = -\alpha\theta \quad (8)$$

$$F_b = \frac{\alpha\theta}{2} \quad (9)$$

$$F_c = \frac{\alpha\theta}{2} \quad (10)$$

Here, because a state with no external force applied to the bendable portion 110-1 is assumed, an evaluation value E that is a total sum of the compressive/tensile forces ($F_a$, $F_b$, $F_c$) applied to all of the wires expressed by the following Expression (11) is equal to zero.

$$E = F_a + F_b + F_c \quad (11)$$

Having described the example in which the bendable portion 110-1 is bent in the +X axis direction with reference to FIG. 7 and FIG. 8, the example may be generalized such that the driving control amounts $d_a$, $d_b$ and $d_c$ for the wires 1a, 1b and 1c when the bendable portion 110-1 is turned by an angle ζ (FIG. 4) about the Z axis in the +X axis direction can be expressed by the following Expressions (12), (13) and (14), respectively.

[Math. 4]

$$d_a = -r_g\theta\cos\zeta \quad (12)$$

$$d_b = -r_g\theta\cos\left(\zeta - \frac{2\pi}{3}\right) \quad (13)$$

$$d_c = -r_g\theta\cos\left(\zeta - \frac{4\pi}{3}\right) \quad (14)$$

Here, the angle ζ will be called a turning angle. The turning angle ζ is defined as an angle in a direction toward the Y axis relative to the X axis on the XY plane, as illustrated in FIG. 4. The bending angle θ is defined as an angle in a direction toward the Z axis with reference to the X axis on the XZ plane as illustrated in FIG. 8. The driving control amounts $d_a$, $d_b$ and $d_c$ for the wires 1a, 1b and 1c expressed by Expressions (12) to (14) above correspond to the driving control amount based on the bending angle command value θ and the turning angle command value ζ.

In this case, the compressive/tensile forces $F_a$, $F_b$ and $F_c$ applied to the wires 1a, 1b and 1c can be expressed by Relational Expressions (15), (16) and (17).

[Math. 5]

$$F_a = -\alpha\theta\cos\zeta \quad (15)$$

$$F_b = -\alpha\theta\cos\left(\zeta - \frac{2\pi}{3}\right) \quad (16)$$

$$F_c = -\alpha\theta\cos\left(\zeta - \frac{4\pi}{3}\right) \quad (17)$$

FIG. 9 is a diagram illustrating changes of compressive/tensile forces $F_a$ to $F_c$ of wires and an evaluation value E when the turning angle ζ is changed with a constant bending angle command value θ under a condition that no external force acts on the bendable portion 110-1 according to the first embodiment of the present invention. More specifically, FIG. 9 illustrates the turning angle ζ on the horizontal axis and the compressive/tensile forces on the vertical axis. As seen from FIG. 9, when no external force acts on the bendable portion 110-1, the evaluation value E that is a total sum of the compressive/tensile forces applied to all of the wires 1a to 1c is equal to zero.

Next, a case where an external force acts on the bendable portion 110-1 in the continuum robot 100 according to the first embodiment will be described.

FIG. 10 is a diagram illustrating time changes of compressive/tensile forces $F_a$ to $F_c$ of the wires and the evaluation value E when the bendable portion 110-1 is bent in an X axis direction (direction of ζ=0) under a condition that an external force acts on the bendable portion 110-1 according to the first embodiment of the present invention. More specifically, FIG. 10 illustrates time on the horizontal axis and the compressive/tensile forces on the vertical axis.

FIG. 11 is a diagram illustrating time changes of the compressive/tensile forces $F_a$ to $F_c$ of the wires and the evaluation value E when the bendable portion 110-1 is bent in a Y axis direction (direction of ζ=π/2) under a condition that the external force acts on the bendable portion 110-1 according to the first embodiment of the present invention. More specifically, FIG. 11 illustrates time on the horizontal axis and the compressive/tensile forces on the vertical axis.

In both of FIG. 10 and FIG. 11, the continuum robot 100 during a period (a) performs a bending operation which linearly changes the bending angle command value θ. During periods (b) to (f), the continuum robot 100 keeps the bending angle command value θ at a constant state. During the periods (c) and (e), sinusoidal external forces mainly containing forces in the X axis direction and the Y axis direction, respectively, are applied. In FIG. 10 and FIG. 11, no external force is applied during periods (b), (d) and (f).

In FIG. 10, during the period (a), the compressive/tensile forces $F_b$ and $F_c$ change linearly in the positive direction, and the compressive/tensile force $F_a$ changes linearly in the negative direction. The evaluation value E that is a total sum of the compressive/tensile force is equal to zero. On the other hand, in FIG. 11, during the period (a), the compressive/tensile force $F_a$ does not change, and the compressive/tensile force $F_b$ changes linearly in the negative direction, and the compressive/tensile force $F_c$ changes linearly in the positive direction. Also in this case, the evaluation value E that is a total sum of the compressive/tensile force is equal to zero. In FIG. 10 and FIG. 11, during periods (c) and (e), the compressive/tensile forces on the wires change relative to the compressive/tensile forces caused by the bending during the period (a), and the evaluation value E also changes.

Next, with reference to FIG. 10 and FIG. 11, a control method will be described which suppresses damage to the continuum robot 100 and an object when an external force is applied from the object to the bendable portion 110-1.

In order to determine whether an external force is applied to the bendable portion 110-1, a method which compares the compressive/tensile forces $F_a$, $F_b$ and $F_c$ applied to the wires 1a, 1b and 1c with a threshold value is effective. The determination here is performed by the threshold value comparing unit 220 illustrated in FIG. 6.

Here, for example, a predetermined threshold value T is used, and, in order to prevent absolute values of the compressive/tensile forces $F_a$, $F_b$ and $F_c$ from exceeding the threshold value T, an alert may be issued to an operator or the driving may be stopped if one or more conditions expressed by the following Expressions (18) to (20) is or are satisfied.

$$|F_a|>T \quad (18)$$

$$|F_b|>T \quad (19)$$

$$|F_c|>T \quad (20)$$

However, as seen from the bending operation during the period (a) in FIG. 10 and FIG. 11, the compressive/tensile forces largely change even when an external force does not act thereon with some bending angle command values θ or turning angle command values ζ. For example, if the threshold value is determined such that the external force acting on the compressive/tensile force $F_a$ during the period (c) when the turning angle ζ=0 (corresponding to the graph in FIG. 10) can be detected, changes of the compressive/tensile forces like the compressive/tensile force $F_a$ when the turning angle ζ=π/2 (corresponding to the graph in FIG. 11) may not be detected.

Accordingly, in the first embodiment of the present invention, as expressed in Expression (21), a total sum of the compressive/tensile forces of the wires is used as the evaluation value E, and, if the absolute value of the evaluation value E exceeds the threshold value (or if Expression (21) is satisfied), it is determined that an excessive external force is being applied.

$$|E|>T \quad (21)$$

In this case, referring to FIG. 10 and FIG. 11, the absolute value of the evaluation value E changes during the periods (c) and (e) when an external force is applied to the bendable portion 110-1 so that the external force can be more accurately detected. As the threshold value T, a value preventing an external force applied to the continuum robot 100 or an object from damaging them may be acquired through an experiment or an analysis, for example.

Although the description above assumes that the continuum robot 100 has three wires 1a to 1c, this may be generalized to a case where N wires are provided therein. In a case where the continuum robot 100 has N wires, a total sum of all compressive/tensile forces $F_i$ (i=1 to N) is used as the evaluation value E, which is then compared with the threshold value T as expressed by Expression (22).

[Math. 6]

$$E = \sum_{i=1}^{N} F_i \quad (22)$$

When the ith (i=1 to N) driving control amount is $d_i$ for driving the continuum robot 100 with the bending angle command value θ and the turning angle command value ζ and when the compressive/tensile forces acting on the wire is $F_i$, the $d_i$ and $F_i$ are expressed by the following Expression (23) and (24). In this case, it is assumed that the wire expressed by i=1 is placed on the X axis, and it is further assumed that all of the wires are arranged at equal intervals on a circumference with a radius $r_g$ about the origin.

[Math. 7]

$$d_i = -r_g \theta \cos\left\{\zeta - \frac{2(i-1)}{N}\pi\right\} \quad (23)$$

$$F_i = -\alpha \theta \cos\left\{\zeta - \frac{2(i-1)}{N}\pi\right\} \quad (24)$$

The generalized case where the continuum robot 100 has N wires will be described below. Although the threshold value T is a constant in Expression (21), the threshold value T may be a function T(θ) of the bending angle command value θ, for example. In this case, T in Expression (21) is replaced by the function T(θ) as in Expression (25).

$$|E| > T(\theta) \quad (25)$$

In a case where no external force is applied, the compressive/tensile force $F_i$ is in proportion to the bending angle command value θ. Therefore, the function T(θ) representing the threshold value may change linearly as expressed by using positive proportionality constants β and γ, for example, as in Expression (26).

$$T(\theta) = -\beta\theta + \gamma \quad (26)$$

In this case, as the bending angle command value θ increases, the threshold value is reduced in consideration of compressive/tensile forces caused by bending so that failures, such as cutting of wires, in the continuum robot 100 can be easily avoided. The threshold value T may be a function T(θ, ζ) of the bending angle command value θ and the turning angle command value ζ, for example.

In a case where no external force is applied and where the compressive/tensile force $F_i(\theta)$ acting on the wires bent based on the bending angle command value θ are known, the evaluation value E may be expressed as follows. That is, in this case, the evaluation value E may be defined as a total sum of a difference between $F_i$ and $F_i(\theta)$ and may be expressed by Expression (27) to remove the influence of the compressive/tensile force caused by a bending operation.

[Math. 8]

$$E = \sum_{i=1}^{N} \{(F_i - F_i(\theta))\} \quad (27)$$

Here, $F_i(\theta)$ in Expression (27) may be calculated by using a kinematics model or may be acquired with reference to information measured in advance, for example.

Having described that the three wires 1a, 1b and 1c are driven and the bending angle command value θ and turning angle command value ζ for the bendable portion 110-1 are changed, embodiments of the present invention are not limited thereto. For example, one wire of the three wires 1a, 1b and 1c may not be driven but be fixed within the support mechanism 120, and the other two wires may be driven, and the bending angle command value θ and turning angle command value ζ therefor may be changed, which is also applicable to the present invention. In other words, according to the present invention, the continuum robot control apparatus 200 controlling an operation of the continuum robot 100 including the bendable portion 110-1 having the plurality of wires 1a to 1c, partial wires 1 of which are driven to bend the bendable portion 110-1 is also applicable.

Having described that the external force estimating unit 210 estimates an external force applied to the bendable portion 110-1 based on the compressive/tensile forces applied to all of the wires 1 of the plurality of wires 1a to 1c, embodiments of the present invention are not limited thereto. Implementation in which the external force estimating unit 210 estimates an external force applied to the bendable portion 110-1 based on a sum of compressive/tensile forces applied to two or more wires 1 is also applicable to the present invention. In this implementation, for example, the external force estimating unit 210 may estimate an external force applied to the bendable portion 110-1 based on a sum of compressive/tensile forces applied to two wires 1 of the three wires 1a to 1c. Implementation in which three or more wires may be applied as the N wires and the external force estimating unit 210 estimates an external force applied to the bendable portion 110-1 based on a sum of tensile forces applied to different combinations of two or more wires of the three or more wires is also applicable to the present invention.

In the continuum robot control apparatus 200 according to the first embodiment, the external force estimating unit 210 estimates an external force applied to the bendable portion 110-1 based on the compressive/tensile forces $F_a$ to $F_c$ applied to the plurality of wires 1a to 1c. The driving control unit 240 controls driving of the wires 1a to 1c to be driven based on the external force estimated by the external force estimating unit 210. More specifically, the driving control unit 240 performs the control to stop the driving of the wires 1a to 1c if the external force estimated by the external force estimating unit 210 exceeds the threshold value.

According to this configuration, reduction of the range for driving the continuum robot 100 can be avoided while damage to the continuum robot 100 and an object can be suppressed.

Second Embodiment

Next, a second embodiment of the present invention will be described. In the following description regarding the second embodiment, descriptions regarding matters common to those of the first embodiment are omitted, but matters different from the first embodiment will be described.

A continuum robot to be used in the second embodiment is the same as the continuum robot 100-1 used in the first embodiment as described with reference to FIG. 1 to FIG. 5. The schematic configuration of the continuum robot control system according to the second embodiment is the same as the schematic configuration of the continuum robot control system 10 according to the first embodiment as illustrated in FIG. 6. In other words, the schematic configuration of a continuum robot control apparatus according to the second embodiment is the same as the schematic configuration of the continuum robot control apparatus 200 according to the first embodiment as illustrated in FIG. 6.

According to the first embodiment, an external force applied to the bendable portion 110 is estimated by using a total sum of the compressive/tensile forces of all of the wires 1a to 1c as the evaluation value E by the external force estimating unit 210, and the threshold value comparing unit 220 compares the external force (evaluation value E) and a threshold value. According to the second embodiment, the evaluation value E to be estimated as an external force is calculated based on the calculated value of the compressive/tensile force $F_i$ of each of the wires, and the evaluation value E and a threshold value are compared.

As an example of the calculation, an evaluation function $E(\lambda)$ is defined as a total sum of moments acting in the direction of rotation from the X axis by an angle $\lambda$ and can be expressed by Expression (28). Based on the evaluation function $E(\lambda)$ expressed by Expression (28), an external force acting in the direction of rotation from the X axis by the angle $\lambda$ can be estimated.

[Math. 9]

$$E(\lambda) = \sum_{i=1}^{N} \left[ F_i r_g \cos\left\{\lambda - \frac{2(i-1)}{N}\pi\right\} \right] \quad (28)$$

Thus, the external force estimating unit 210 can estimate an external force applied in the direction (specific direction) orthogonal to the direction of bending of the bendable portion 110-1, for example. The external force in the direction orthogonal to the direction of bending of the bendable portion 110-1 is a force acting in the direction for twisting the bendable portion 110-1 about the Z axis. Because of this calculation, damage to the continuum robot 100-1 due to the torsion can be avoided. The torsion causes an error of the turning angle $\zeta$ when the bendable portion 110-1 is bent. Suppression of such torsion can be achieved by using a threshold value as in this embodiment, which may effectively prevent accuracy of the driving from degrading.

The comparison between the evaluation function $E(\lambda)$ expressed by Expression (28) and a threshold value will be described below with reference to the continuum robot 100-1 including the bendable portion 110-1 having the three wires 1a to 1c as used in the first embodiment.

FIG. 12 illustrates time changes of compressive/tensile forces $F_a$ to $F_c$ of the wires and the evaluation value E when the bendable portion 110-1 is bent in the X axis direction (direction of $\zeta=0$) under a condition that an external force is acting on the bendable portion 110-1 according to the second embodiment of the present invention. More specifically, FIG. 12 illustrates time on the horizontal axis and compressive/tensile forces on the vertical axis.

FIG. 12 schematically illustrates time changes of the compressive/tensile forces $F_a$, $F_b$, and $F_c$ of the wires 1a to 1c in a case where, after the bendable portion bends in the X axis direction (direction of $\zeta=0$) as in FIG. 10, an external force is received by the wires 1a to 1c in the X axis direction during a period (c) and an external force is received by the wires 1a to 1c in the Y axis direction during a period (e). When the value of the angle $\lambda$ is $\pi/2$ that is a direction orthogonal to the bending direction of the bendable portion 110-1, the following relationship expressed by Expression (29) is obtained.

[Math. 10]

$$E\left(\frac{\pi}{2}\right) = \frac{\sqrt{3}}{2}(F_b - F_c)r_g \quad (29)$$

In this case, $E(\pi/2)$ has a value which does not change during the period (c) when an external force is received in the X axis direction and has a value which changes during the period (e) when an external force is received in the Y axis direction, as illustrated in FIG. 12. Therefore, when the bendable portion 110-1 is bent in the X axis direction (direction of $\zeta=0$), the threshold value comparing unit 220 compares $E(\pi/2)$ with the threshold value so that an external force applied in the direction orthogonal to the direction of bending of the bendable portion 110-1 can be detected.

FIG. 13 illustrates time changes of the compressive/tensile forces $F_a$ to $F_c$ of the wires and the evaluation value E when the bendable portion 110-1 is bent in the Y axis direction (direction of $\zeta=\pi/2$) under a condition that the external force is acting on the bendable portion 110-1 according to the second embodiment of the present invention. More specifically, FIG. 13 illustrates time on the horizontal axis and the compressive/tensile force on the vertical axis.

FIG. 13 schematically illustrates time changes of the compressive/tensile forces $F_a$, $F_b$, and $F_c$ of the wires 1a to 1c in a case where, after the bendable portion bends in the Y axis direction (direction of $\zeta=\pi/2$) as in FIG. 11, an external force is received by the wires 1a to 1c in the X axis direction during a period (c) and an external force is received by the wires 1a to 1c in the Y axis direction during a period (e). When the value of the angle $\lambda$ is $\pi$ that is a direction orthogonal to the bending direction of the bendable portion 110-1, the following relationship expressed by Expression (30) is obtained.

[Math. 11]

$$E(\pi) = \left(-F_a + \frac{F_b}{2} + \frac{F_c}{2}\right)r_g \quad (30)$$

In this case, $E(\pi)$ has a value which does not change during the period (e) when an external force is received in the Y axis direction and has a value which changes during the period (c) when an external force is received in the X axis direction, as illustrated in FIG. 13. Therefore, when the bendable portion 110-1 is bent in the Y axis direction (direction of $\zeta=\pi/2$), the threshold value comparing unit 220 compares $E(\pi)$ with a threshold value so that an external force applied in the direction orthogonal to the direction of bending of the bendable portion 110-1 can be detected.

As a result, by substituting the following Expression (31) into the evaluation function $E(\lambda)$ and by comparing the following Expression (32) with a threshold value, an external force applied in the direction orthogonal to the direction of bending of the bendable portion 110-1 can be detected.

[Math. 12]

$$\lambda = \zeta + \frac{\pi}{2} \quad (31)$$

$$E\left(\zeta + \frac{\pi}{2}\right) = \sum_{i=1}^{N}\left[F_i r_g \cos\left\{\zeta + \frac{\pi}{2} - \frac{2(i-1)}{N}\pi\right\}\right] \quad (32)$$

In Expression (28), the value of the compressive/tensile force $F_b$ and the value of the compressive/tensile force $F_c$ are used for the threshold value comparison. When the direction of bending of the bendable portion 110-1 is predetermined like the case above, the compressive/tensile forces of all of the wires may not be used. In this case, the compressive/tensile forces of wires for the bending may be used, or the direction for driving may be determined based on wires the compressive/tensile forces of which are detected.

In a case where there are many wires the compressive/tensile forces of which are to be detected, the compressive/tensile forces of all of the wires may not be detected, but the number of wires for the detection may be reduced within a range that does not affect the threshold determination. In this case, for example, when the number of wires N is even, the evaluation function E may be defined as a total sum of compressive/tensile forces of even-numbered wires, and the following Expression (33) may be compared with the threshold value.

[Math. 13]

$$E = \sum_{i=1}^{N/2} F_{2i-1} \quad (33)$$

The method for selecting wires the compressive/tensile force of which are to be detected is not limited to those described herein but the wires may be selected in consideration of an external force to be measured or accuracy of the measurement.

According to the second embodiment, reduction of the range for driving the continuum robot 100 can be avoided while damage to the continuum robot 100 and an object can be suppressed, like the first embodiment.

Third Embodiment

Next, a third embodiment of the present invention will be described. In the following description regarding the third embodiment, descriptions regarding matters common to those of the first and second embodiments are omitted, but matters different from the first and second embodiments will be described.

The continuum robot used in the third embodiment is the same as the continuum robot 100-1 used in the first embodiment illustrated in FIG. 1 to FIG. 5. The schematic configuration of the continuum robot control system according to the third embodiment is the same as the schematic configuration of the continuum robot control system 10 according to the first embodiment as illustrated in FIG. 6. In other words, the schematic configuration of a continuum robot control apparatus according to the third embodiment is the same as the schematic configuration of the continuum robot control apparatus 200 according to the first embodiment as illustrated in FIG. 6.

Although the first embodiment and second embodiment do not consider an influence of friction occurring at the wires on the compressive/tensile forces, the third embodiment estimates an external force in consideration of an influence of the friction occurring at the wires.

FIG. 14 is a diagram illustrating time changes of compressive/tensile forces $F_a$ to $F_c$ of wires and the evaluation value E when a bendable portion 110-1 bends in an X axis direction (direction of $\zeta=0$) and receives an external force in a system considering friction of the bendable portion 110-1 according to the third embodiment of the present invention. More specifically, FIG. 14 illustrates time on the horizontal axis and compressive/tensile forces on the vertical axis.

Referring to FIG. 14, during a period (a), the continuum robot 100 performs a bending operation which linearly changes the bending angle command value θ. During periods (b) to (f), the bending angle command value θ is kept at a constant state. During the periods (c) and (e), sinusoidal external forces mainly containing forces in the X axis direction and the Y axis direction, respectively, are applied. Referring to FIG. 14, no external force is applied during periods (b), (d) and (f).

In this system considering friction as illustrated in FIG. 14, the compressive/tensile forces $F_a$ to $F_c$ acting on the wires 1a to 1c are affected by frictional force while the orientation of the frictional force depends on the orientation of an increase or a decrease of the compressive/tensile forces. Therefore, during the periods (b), (d) and (f) in FIG. 14, although no external force is applied, the compressive/tensile forces $F_a$ to $F_c$ have different values depending on the orientation of the force having acted immediately before application of an external force is stopped. Because the values change in accordance with change histories of frictional forces applied to the compressive/tensile forces $F_a$ to $F_c$, the total sum of the compressive/tensile forces $F_a$ to $F_c$ is not equal to zero even when an external force is not applied thereto.

Accordingly, in a system considering friction, a value acquired by compensating an influence of the friction occurring at the wires based on the change histories of the compressive/tensile forces may be estimated as a value of an external force and may be compared with a threshold value. In this case, for example, the compressive/tensile force $F_i$ is corrected (compensated) by the following Expression (34) to acquire $F_i'$.

$$F_i' = F_i - \sigma_i(t) * F_\mu \quad (34)$$

In this case, $\sigma_i(t)$ in Expression (34) depends on the sign of the time change rate $dF_i/dt$ of the compressive/tensile force and can be expressed by following Expression (35).

[Math. 14]

$$\sigma_i(t) = \begin{cases} 1 & \text{if } \frac{dF_i}{dt} > 0 \\ \sigma_i(t - \Delta t) & \text{if } \frac{dF_i}{dt} = 0 \\ -1 & \text{if } \frac{dF_i}{dt} < 0 \end{cases} \quad (35)$$

In Expression (34), $F_i'$ is acquired by adding, as a correction value (compensation value), a value acquired by multiplying a sign $\delta_i(t)$ representing the orientation of friction determined from the time change rate of the compressive/tensile forces by a magnitude $F_\mu$ of frictional force to $F_i$ to remove an influence of the friction. If $dF_i/dt=0$, the orientation affected by friction does not change. Therefore, the immediately preceding $\sigma_i(t-\Delta t)$ may be referred. The magnitude $F_\mu$ may be acquired by an experiment, for example. In this case, an evaluation value E' that is a total sum of the corrected (compensated) compressive/tensile forces $F_i'$ can be expressed by Expression (36).

[Math. 15]

$$E' = \sum_{i=1}^{N} F_i' \qquad (36)$$

FIG. 15 is a diagram illustrating time changes of compressive/tensile forces $F_a'$ to $F_c'$ and an evaluation value E' corrected (compensated) by using Expression (34) to Expression (36) in the system considering friction at the bendable portion 110-1 according to the third embodiment of the present invention.

As seen from FIG. 15, the evaluation value E' that is a total sum of the corrected (compensated) compressive/tensile forces is equal to zero during periods (b), (d) and (f) with no external force applied. Thus, also according to the third embodiment, the continuum robot control method used in the first embodiment and the second embodiment may be used for the threshold value comparison.

According to the third embodiment, the external force estimating unit 210 may estimate, as an external force, the evaluation value E' acquired by compensating an influence of friction occurring at the wires on the compressive/tensile forces $F_a$ to $F_c$ of the wires 1a to 1c. The threshold value comparing unit 220 may compare the external force (evaluation value E') estimated by the external force estimating unit 210 with a threshold value to determine whether the external force exceeds the threshold value or not. According to this configuration, because an influence of friction occurring at the wires is also considered, reduction of the range for driving the continuum robot 100 can be avoided while damage to the continuum robot 100 and an object can further be suppressed.

Fourth Embodiment

Next, a fourth embodiment of the present invention will be described. In the following description regarding the fourth embodiment, descriptions regarding matters common to those of the first to third embodiments are omitted, but matters different from the first to third embodiments will be described.

FIG. 16 is a diagram illustrating an example of an outer appearance configuration of a continuum robot 100 according to the fourth embodiment of the present invention. Hereinafter, the continuum robot 100 illustrated in FIG. 16 will be called a "continuum robot 100-4A" as required. FIG. 16 illustrates an XYZ coordinate system in a three-dimensional space. In FIG. 1 to FIG. 5 and FIG. 16, like numbers refer to like parts, and any repetitive detail descriptions will be omitted.

According to the first to third embodiment, as illustrated in FIG. 1, an operation to be performed by the continuum robot 100-1 having one bendable portion 110-1 is controlled. On the other hand, according to the fourth embodiment, as illustrated in FIG. 16, an operation to be performed by the continuum robot 100-4A having a bendable portion group 110-4 including a plurality of (more specifically three in the example illustrated in FIG. 16) bendable portions 110-1 to 110-3 that are serially connected is controlled. More specifically, the continuum robot 100-4A illustrated in FIG. 16 includes, in decreasing order of the values on the Z coordinate in the +Z axis direction, a bendable portion 110-3, a bendable portion 110-2 and a bendable portion 110-1 that are serially connected.

The bendable portion 110-3 bends in response to driving of three wires 3a, 3b and 3c. The wires 3a to 3c have ends in the +Z axis direction bonded and fixed to different positions of a tip member 115 and have ends in the −Z axis direction connected to the compressive/tensile force detecting units (corresponding to 121 in FIG. 2) and driving units (corresponding to 122 in FIG. 2) within the support mechanism 120. In this case, one compressive/tensile force detecting unit and one driving unit are provided for each of the wires. The bendable portion 110-3 includes the tip member 115 and a plurality of guiding members 116. In the example illustrated in FIG. 16, the bendable portion 110-3 extends from a tip member end 115e that is an end in the +Z axis direction of the tip member 115 to a tip member end 113e that is an end in the +Z axis direction of the tip member 113 in the bendable portion 110-2.

The tip member 115 has a ring shape with the Z axis direction as a center axis, and the wires 3a to 3c are bonded and fixed at positions different from each other in the tip member 115, as illustrated in FIG. 16. Each of the guiding members 116 has a ring shape with the Z axis direction as a center axis as illustrated in FIG. 16. Each of the guiding members 116 has a fixing hole 1121 and guiding holes 1122b and 1122c, which are through-holes in the Z axis direction, like the guiding member 112 according to the first embodiment illustrated in FIG. 3 and FIG. 4. The wire 3a is fixed to the fixing hole 1121 of the guiding member 116, and the wires 3b and 3c extend through the guiding holes 1122b and 1122c of the guiding member 116.

The bendable portion 110-2 basically has the same structure as that of the bendable portion 110-3 but the tip member 113 and guiding member 114 included in the bendable portion 110-2 further have guiding holes through which the wires 3a to 3c slidably extend in the bendable portion 110-3. The bendable portion 110-2 bends in response to driving of three wires 2a, 2b and 2c bonded and fixed at different positions of the tip member 113. Because of space limitations, FIG. 16 does not illustrate the three wires 2a to 2c. The three wires 2a to 2c have ends in the −Z axis direction connected to the compressive/tensile force detecting units (corresponding to 121 in FIG. 2) and driving units (corresponding to 122 in FIG. 2) within the support mechanism 120. In this case, one compressive/tensile force detecting unit and one driving unit are provided for each of the wires. In the example illustrated in FIG. 16, the bendable portion 110-2 extends from a tip member end 113e that is an end in the +Z axis direction of the tip member 113 to a tip member end 111e that is an end in the +Z axis direction of the tip member 111 in the bendable portion 110-1.

The bendable portion 110-1 illustrated in FIG. 16 corresponds to the bendable portion 110-1 illustrated in FIG. 1, for example, but the tip member 111 and guiding member 112 illustrated in FIG. 16 further have guiding holes through which the wires 3a to 3c in the bendable portion 110-3 and the wires 2a to 2c in the bendable portion 110-2 slidably extend.

The internal configuration of the support mechanism 120 according to the fourth embodiment may be the same as the internal configuration of the support mechanism 120 according to the first embodiment illustrated in FIG. 2. According to the fourth embodiment, one compressive/tensile force detecting unit 121 and one driving unit 122 are provided for each of a total of nine wires of the wires 1a to 1c, the wires 2a to 2c and the wires 3a to 3c at respective ends in the −Z axis direction. Thus, the compressive/tensile force applied to each of the wires can be detected.

The schematic configuration of the continuum robot control system according to the fourth embodiment is the same as the schematic configuration of the continuum robot control system 10 according to the first embodiment illustrated in FIG. 6. In other words, the schematic configuration of the continuum robot control apparatus according to the fourth embodiment is the same as the schematic configuration of the continuum robot control apparatus 200 according to the first embodiment illustrated in FIG. 6.

Generalizing the configuration for the following descriptions, the continuum robot 100 has S bendable portions. In the continuum robot 100, Ns wires are provided in the sth (s=1 to S) bendable portion from an end close to the support mechanism 120. In this case, a compressive/tensile force $F_{s,i}$ is applied to the ith (i=1 to Ns) wire of the sth bendable portion. Here, an evaluation value Es that is a total sum of the com-pressive/tensile forces in each of the bendable portions can be expressed as Expression (37).

[Math. 16]

$$E_s = \sum_{i=1}^{N_s} F_{s,i} \tag{37}$$

For example, a case will be discussed in which the sth bendable portion is bent with no external force applied thereto. In this case, the tip member and guiding member of the sth bendable portion receives reaction moment from wires in the s+1th to Sth bendable portions. The wires in the sth bendable portion receive reaction moment from the tip members and guiding members of the first to s−1th bendable portions.

Assuming that friction between the wires and the tip members and the guiding members is ignorable, the sth bendable portion does not receive a translational force from the other bendable portions, and the total compressive/tensile force applied to the Ns wires do not change though the corresponding compressive/tensile force changes due to the reaction moment.

Next, a case with an external force applied to the continuum robot 100 will be discussed.

When an external force is applied to the sth bendable portion, an evaluation value Es that is a total sum of the compressive/tensile forces changes. On the other hand, when an external force acts on the s+1th to Sth bendable portion, reaction moment acts on the tip member and guiding member of the sth bendable portion through the wires in the s+1th to Sth bendable portions. Also, when an external force acts on the first to s−1th bendable portions, reaction moment is applied to the wires in the sth bendable portion through the tip members and guiding members in the first to s−1th bendable portions. Also in this case, no translational force occurs, and the total compressive/tensile forces applied to the Ns wires do not change though the compressive/tensile force $F_{s,i}$ changes due to the reaction moment.

As described above, when an external force is applied to the sth bendable portion, the evaluation value Es that is a total sum of the compressive/tensile forces changes but Et (t≠s) in the bendable portions excluding the sth bending portion does not change. Therefore, the evaluation value Es that is a total sum of the compressive/tensile forces of each of the bendable portions is compared with a threshold value so that a force of each of the bendable portions acting on an object can be estimated and that damage to the object can be avoided. In other words, in this case, the external force estimating unit 210 may estimate an external force (evaluation value Es) to each bendable portion of the plurality of bendable portions. The threshold value comparing unit 220 may compare the external force (evaluation value Es) estimated for each of the bendable portions with the threshold value. The alert generating unit 230 may perform alerting processing for each bendable portion of the plurality of bendable portions, and the driving control unit 240 controls driving of wires to be driven in each bendable portion of the plurality of bendable portions.

The compressive/tensile force $F_{s,i}$ acting on each wire is influenced by interactions between bendable portions. Accordingly, the external force estimating unit 210 and the threshold value comparing unit 220 compare the compressive/tensile force $F_{s,i}$ as well as the evaluation value Es that is a total sum of compressive/tensile forces with the threshold value so that damage to the continuum robot 100 can more easily be avoided.

FIG. 17 illustrates another example of the outer appearance configuration of the continuum robot 100 according to the fourth embodiment of the present invention. Hereinafter, the continuum robot 100 illustrated in FIG. 17 will be called a "continuum robot 100-4B" as required. FIG. 17 illustrates an XYZ coordinate system in a three-dimensional space. In FIG. 17 and FIG. 1 and FIG. 16, like numbers refer to like parts, and any repetitive detail descriptions will be omitted.

More specifically, the continuum robot 100-4B illustrated in FIG. 17 further includes a long bendable member 130 and a long-bendable-member force detecting unit 140 between the bendable portion group 110-4 and the support mechanism 120, compared with the continuum robot 100-4A illustrated in FIG. 16.

The long bendable member 130 is a porous tube having holes through which wires of the bendable portion group 110-4 are made slide and are guided. In this case, the bendable portion group 110-4 and the long bendable member 130 are capable of sliding. Therefore, when an external force is applied to one of them, no translational force occurs but reaction moment occurs at the other. Therefore, also in the case of the continuum robot 100-4B illustrated in FIG. 17, the evaluation value Es that is a total sum of compressive/tensile forces in each of the bendable portion 110-1 to 110-3 of the bendable portion group 110-4 may be compared with a threshold value, like the continuum robot 100-4A illustrated in FIG. 16. Furthermore, in the case of the continuum robot 100-4B illustrated in FIG. 17, the external force estimating unit 210 and the threshold value comparing unit 220 may compare a force acting on the long bendable member 130, which is detected by the long-bendable-member force detecting unit 140, with a threshold value.

According to the fourth embodiment, reduction of the range for driving the continuum robot 100 can be avoided while damage to the continuum robot 100 and an object can be suppressed, like the first embodiment.

Fifth Embodiment

Next, a fifth embodiment of the present invention will be described. In the following description regarding the fifth embodiment, descriptions regarding matters common to those of the first to fourth embodiments are omitted, but matters different from the first to fourth embodiments will be described.

FIG. 18 is a diagram illustrating an example of an outer appearance configuration of a continuum robot 100 according to a fifth embodiment of the present invention. Hereinafter, the continuum robot 100 illustrated in FIG. 18 will be called a "continuum robot 100-5" as required. FIG. 18 illustrates an XYZ coordinate system in a three-dimensional space. In FIG. 1 to FIG. 5 and FIG. 18, like numbers refer to like parts, and any repetitive descriptions will be omitted.

FIG. 19 is a cross section view taken at an XZ plane of the continuum robot 100-5 illustrated FIG. 18. In FIG. 18 and FIG. 19, like numbers refer to like parts.

The continuum robot 100-5 illustrated in FIG. 18 includes a plurality of wires 1-1 to 1-4, a bendable portion 110-5, a support mechanism 120, and a bendable-portion force detecting unit 150. In the continuum robot 100-5, the bendable portion 110-5 bends in response to driving of a plurality of wires 1-1 to 1-4.

The bendable portion 110-5 has a cylindrical shape with the Z axis as a center axis, as illustrated in FIG. 18 and FIG. 19. The bendable portion 110-5 has elastic connecting units 118 arranged alternately as illustrated in FIG. 18 and FIG. 19. Each of the elastic connecting units 118 has an elastic hinge structure 117 which deform in the XZ plane or the YZ plane so that the bendable portion 110-5 can three-dimensionally deform. The bendable portion 110-5 is mechanically connected to the support mechanism 120, and the bendable-portion force detecting unit 150 is capable of detecting a force $F_S$ applied to the bendable portion 110-5. Here, the bendable-portion force detecting unit 150 is configured to detect a force $F_S$ received by the bendable portion 110-5 at its a proximal end part. Each of the elastic connecting units 118 may often be made of a hyperelastic material but may have a bending structure which has a plurality of members connected by rivets, for example, and can rotate about the rivets. Alternatively, each of the elastic connecting units 118 may have a flexible tube-shaped structure.

The wires 1-1 to 1-4 are arranged in parallel with the Z axis, as illustrated in FIG. 18 and have their ends in the +Z axis direction bonded and fixed at different positions of a tip 117e of the elastic hinge structure in the elastic connecting unit 118. Although FIG. 18 illustrate four wires 1-1 to 1-4, at least one wire may be provided for driving the bendable portion 110-5 within a plane, and at least two or more wires may be provided for driving the bendable portion 110-5 three-dimensionally.

The internal configuration of the support mechanism 120 according to the fifth embodiment may be the same as the internal configuration of the support mechanism 120 according to the first embodiment illustrated in FIG. 2. According to the fifth embodiment, one compressive/tensile force detecting unit 121 and one driving unit 122 are provided for each of the wires 1-1 to 1-4 at respective ends in the −Z axis direction. Thus, compressive/tensile forces $F_1$, $F_2$, $F_3$, and $F_4$ applied to the wires can be detected. The elastic connecting units 118 have guiding holes through which the wires 1-1 to 1-4 are made slide and are guided, and the wires 1-1 to 1-4 fixed to the tip 117e extend through the guiding holes.

The schematic configuration of the continuum robot control system according to the fifth embodiment is the same as the schematic configuration of the continuum robot control system 10 according to the first embodiment illustrated in the FIG. 6. In other words, the schematic configuration of the continuum robot control apparatus according to the fifth embodiment is the same as the schematic configuration of the continuum robot control apparatus 200 according to the first embodiment illustrated in FIG. 6 described above.

Next, a case where the bendable portion 110-5 is bent with no external force applied to the bendable portion 110-5 will be discussed. Defining a total sum of the compressive/tensile forces $F_1$, $F_2$, $F_3$, and $F_4$ of the wires and a force $F_S$ detected by the bendable-portion force detecting unit 150 as an evaluation value E, the evaluation value E can be expressed by the following Expression (38).

$$E = F_1 + F_2 + F_3 + F_4 + F_S \quad (38)$$

In this case, the force received by the bendable portion 110-5 through the wires 1 is balanced with the force received by the support mechanism 120 from the bendable portion 110-5, the evaluation value E expressed by Expression (38) is equal to zero. On the other hand, when an external force acts on the bendable portion 110-5, the evaluation value E that is a total sum of the compressive/tensile forces $F_1$, $F_2$, $F_3$, and $F_4$ of the wires 1 and the force $F_S$ detected by the bendable-portion force detecting unit 150 is not equal to zero and can be compared with a threshold value.

According to the fifth embodiment, reduction of the range for driving the continuum robot 100 can be avoided while damage to the continuum robot 100 and an object can be suppressed, like the first embodiment.

Sixth Embodiment

Next, a sixth embodiment of the present invention will be described. In the following description regarding the sixth embodiment, descriptions regarding matters common to those of the first to fifth embodiments are omitted, but matters different from the first to fifth embodiments will be described.

FIG. 20 is a diagram illustrating an example of an outer appearance configuration of a continuum robot 100 according to a sixth embodiment of the present invention. Hereinafter, the continuum robot 100 illustrated in FIG. 20 will be called a "continuum robot 100-6" as required. FIG. 20 illustrates an XYZ coordinate system in a three-dimensional space. In FIG. 1 to FIG. 5 and FIG. 20, like numbers refer to like parts, and any repetitive detail description will be omitted.

FIG. 21 is a cross section view taken at an XZ plane of the continuum robot 100-6 illustrated in FIG. 20. In FIG. 20 and FIG. 21, like numbers refer to like parts.

More specifically, the continuum robot 100-6 illustrated in FIG. 20 further includes an outer cover structure 119G and an inner cover structure 119N that protect the bendable portion 110, in addition to the continuum robot 100-1 illustrated in FIG. 1. Hereinafter, the bendable portion 110 further including the outer cover structure 119G and the inner cover structure 119N will be called a "bendable portion 110-6".

The outer cover structure 119G and the inner cover structure 119N are fixed to a side surface of the tip member 111 at the end in the +Z axis direction and slidably cover the support mechanism 120 at the end in the −Z axis direction.

The internal structure of the support mechanism 120 according to the sixth embodiment may be the same as the internal structure of the support mechanism 120 according to the first embodiment illustrated in FIG. 2. The schematic configuration of the continuum robot control system according to the sixth embodiment is the same as the schematic configuration of the continuum robot control system 10 according to the first embodiment illustrated in FIG. 6 described above. In other words, the schematic configuration of the continuum robot control apparatus according to the sixth embodiment is the same as the schematic configuration of the continuum robot control apparatus 200 according to the first embodiment illustrated in FIG. 6 described above.

In the continuum robot 100-6 illustrated in FIG. 20 and FIG. 21, when the bendable portion 110-6 is bent with no external force acting thereon, the wires 1a to 1c receive reaction moment but does not receive a translational force from the outer cover structure 119G and the inner cover structure 119N. The evaluation value E that is a total sum of the compressive/tensile forces ($F_a$, $F_b$, $F_c$) acting on all of the wires expressed by Expression (11) is equal to zero. On the other hand, when an external force acts on the wires, the evaluation value E changes and therefore can be compared with a threshold value.

In the continuum robot 100-6 illustrated in FIG. 20, when the outer cover structure 119G and the inner cover structure 119N are fixed to the support mechanism 120 at its end in the −Z axis direction, the bendable-portion force detecting unit 150 provided in the support mechanism 120, for example, may detect a force $F_S$ received by the outer cover structure 119G and the inner cover structure 119N, like the continuum robot 100-5 illustrated in FIG. 18, so that the threshold comparison using Expression (38) can be performed.

The threshold value comparison method is also applicable to other structures than the structure of the continuum robot 100 according to this embodiment. For example, a sum $F_d$ of the compressive/tensile forces received by all of the wires provided for driving the bendable portion 110 and a sum of forces $F_S$ received by a structure included in the bendable portion 110 on the support mechanism 120 side may be used so that an evaluation value E expressed by the following Expression (39) can be compared with the threshold value.

$$E = F_d + F_S \qquad (39)$$

According to the sixth embodiment, reduction of the range for driving the continuum robot 100 can be avoided while damage to the continuum robot 100 and an object can be suppressed, like the first embodiment.

Other Embodiments

The present invention can be realized by processing including supplying a program implementing one or more functions of the aforementioned embodiments to a system or an apparatus over a network or through a computer readable storage medium and reading and executing the program by one or more processors in a computer in the system or the apparatus. The present invention is also realized by a circuit (such as an ASIC) implementing the one or more functions.

The program and a computer readable storage medium storing the program are included in the present invention.

All of the aforementioned embodiments of the present invention merely illustrate examples embodying the present invention, and the technical scope of the present invention should not be interpreted limitedly thereby. In other words, the present invention may be implemented in various forms without departing from the technical spirit and main features of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-071076, filed Apr. 2, 2018, which is hereby incorporated by reference herein in its entirety.

REFERENCE SIGNS LIST

10 Continuum robot control system
100 Continuum robot
1a to 1c Wires
110 Bendable portion
111 Tip member
112 Guiding member
120 Support mechanism
121 Compressive/tensile force detecting unit
122 Driving unit
200 Continuum robot control apparatus
210 External force estimating unit
220 Threshold value comparing unit
230 Alert generating unit
240 Driving control unit
300 Input device

The invention claimed is:

1. A continuum robot control apparatus controlling an operation of a continuum robot having:
a bendable portion bending in response to driving of a plurality of wires;
a support mechanism for guiding the plurality of wires and supporting the bendable portion;
a driver included in the support mechanism and configured to drive the plurality of wires; and
tensile force detector included in the support mechanism and each provided to at least two or more wires of the plurality of wires,
the continuum robot control apparatus comprising:
one or more memories that stores instructions; and
one or more processors that executes the instructions cause the continuum robot apparatus to perform:
estimating an external force applied to the bendable portion based on tensile forces applied to the at least two or more wires of the plurality of wires detected by the tensile force detector; and
driving of the at least two or more wires to be driven based on the external force estimated in the estimating,
wherein in the estimating the external force is estimated based on a sum of tensile forces, each of which is applied to a wire of the at least two or more wires.

2. The continuum robot control apparatus according to claim 1, wherein, in the controlling, a control to stop driving of the at least two or more wires to be driven is performed in a case where the estimated external force exceeds a threshold value.

3. The continuum robot control apparatus according to claim 1, wherein the at least two or more wires are all wires of the plurality of wires.

4. The continuum robot control apparatus according to claim 1,
wherein the plurality of wires are three or more wires, and
wherein, in the estimating, the external force is estimated based on a sum of tensile forces applied to different combinations of the at least two or more wires of the three or more wires.

5. The continuum robot control apparatus according to claim 1, wherein, in the estimating, as the external force, an external force applied in a specific direction of the bendable portion is estimated.

6. The continuum robot control apparatus according to claim 5, wherein the specific direction is a direction orthogonal to a direction of the bending of the bendable portion.

7. The continuum robot control apparatus according to claim 1, wherein the tensile force has a value acquired by compensating an influence of friction occurring at each wire of the at least two or more wires.

8. The continuum robot control apparatus according to claim 1,
wherein the continuum robot has a plurality of bendable portions being serially connected to each other,
wherein, in the estimating, the external force for each bendable portion of the plurality of bendable portions is estimated, and
wherein, in the controlling, driving of the at least two or more wires to be driven is controlled for bending each bendable portion of the plurality of bendable portions.

9. The continuum robot control apparatus according to claim 1, wherein, in the estimating, the external force is estimated based on a sum of tensile forces applied to the at least two or more wires and a force received by the bendable portion at its proximal end part.

10. The continuum robot control apparatus according to claim 1, further comprising an alert generator configured to alert in a case where the external force estimated in the estimating exceeds a threshold value.

11. The continuum robot control apparatus according to claim 1, wherein, in the controlling, driving of the at least two or more wires to be driven is controlled based on a command value relating to a bending angle of the bendable portion and a command value relating to a turning angle of the bendable portion in a case where the external force estimated in the estimating does not exceed a threshold value.

12. A continuum robot control method controlling an operation of a continuum robot having:
a bendable portion bending in response to driving of a plurality of wires;
a support mechanism for guiding the plurality of wires and supporting the bendable portion;
a driver included in the support mechanism and configured to drive the plurality of wires; and
tensile force detector included in the support mechanism and each provided to at least two or more wires of the plurality of wires,
the continuum robot control method comprising:
estimating an external force applied to the bendable portion based on tensile forces applied to the at least two or more wires of the plurality of wires detected by the tensile force detector; and
controlling driving of the at least two or more wires to be driven based on the external force estimated by the estimating,
wherein, in the estimating, the external force is estimated based on a sum of the tensile forces, each of which is applied to a wire of the at least two or more wires.

13. The continuum robot control method according to claim 12, wherein, in the controlling, a control is performed to stop driving of the at least two or more wires to be driven in a case where the external force estimated in the estimating exceeds a threshold value.

14. The continuum robot control method according to claim 12, wherein the at least two or more wires are all wires of the plurality of wires.

15. The continuum robot control method according to claim 12,
wherein the plurality of wires are three or more wires, and
wherein the estimating estimates the external force based on a sum of tensile forces applied to different combinations of the at least two or more wires of the three or more wires.

16. The continuum robot control method according to claim 12, wherein, in the estimating, as the external force, an external force applied in a specific direction of the bendable portion is estimated.

17. The continuum robot control method according to claim 16, wherein the specific direction is a direction orthogonal to a direction of the bending of the bendable portion.

18. The continuum robot control method according to claim 12, wherein the tensile force has a value acquired by compensating an influence of friction occurring at each wire of the at least two or more wires.

19. The continuum robot control method according to claim 12,
wherein the continuum robot has a plurality of bendable portions being serially connected to each other,
wherein, in the estimating the external force is estimated for each bendable portion of the plurality of bendable portions, and
wherein, in the controlling, driving of the at least two or more wires to be driven is controlled for bending each bendable portion of the plurality of bendable portions.

20. The continuum robot control method according to claim 12, wherein the estimating estimates the external force based on a sum of tensile forces applied to the at least two or more wires and a force received by the bendable portion at its proximal end part.

21. The continuum robot control method according to claim 12, further comprising alerting in a case where the external force estimated in the estimating exceeds a threshold value.

22. The continuum robot control method according to claim 12, wherein, in the controlling, driving of the at least two or more wires to be driven is controlled based on a command value relating to a bending angle of the bendable portion and a command value relating to a turning angle of the bendable portion in a case where the external force estimated in the estimating does not exceed a threshold value.

23. A computer readable medium having stored thereon software instructions that, when executed by a processor, cause the processor to perform the estimating and controlling according to claim 1.

* * * * *